US 8,454,923 B2

(12) United States Patent
Haddon

(10) Patent No.: US 8,454,923 B2
(45) Date of Patent: Jun. 4, 2013

(54) CONTINUOUS EXTRACTION TECHNIQUE FOR THE PURIFICATION OF CARBON NANOMATERIALS

(75) Inventor: Robert C. Haddon, Riverside, CA (US)

(73) Assignee: Carbon Solutions, Inc., Riverside, CA (US)

( * ) Notice: Subject to any disclaimer, the term of this patent is extended or adjusted under 35 U.S.C. 154(b) by 218 days.

(21) Appl. No.: 12/969,534

(22) Filed: Dec. 15, 2010

(65) Prior Publication Data

US 2011/0110842 A1    May 12, 2011

Related U.S. Application Data

(63) Continuation-in-part of application No. 12/813,239, filed on Jun. 10, 2010.

(60) Provisional application No. 61/185,952, filed on Jun. 10, 2009.

(51) Int. Cl.
*D01F 9/12* (2006.01)

(52) U.S. Cl.
USPC ............ 423/447.1; 423/447.3; 977/945; 977/952

(58) Field of Classification Search
USPC . 423/447.1, 447.3, 445 B, DIG. 40; 977/745, 977/750, 752, 472
See application file for complete search history.

(56) References Cited

U.S. PATENT DOCUMENTS

| 2,526,782 | A | 10/1950 | Thorpe |
| 2,687,794 | A | 8/1954 | Koch |
| 2,699,852 | A | 1/1955 | Cost |
| 4,167,538 | A | 9/1979 | Taniguchi et al. |
| 5,424,054 | A | 6/1995 | Bethune et al. |

(Continued)

FOREIGN PATENT DOCUMENTS

| CN | 101047086 | 10/2007 |
| EP | 1061040 | 12/2000 |

(Continued)

OTHER PUBLICATIONS

Application of Centrifugation to the Large-Scale Purification of Electric Arc-Produced Single-Walled Carbon Nanotubes Aiping Yu,†, Elena Bekyarova,†,‡, Mikhail E. Itkis,†, Danylo Fakhrutdinov,‡, Robert Webster,† and, and Robert C. Haddon,† Journal of the American Chemical Society 2006 128 (30), 9902-9908.*

(Continued)

*Primary Examiner* — Stuart Hendrickson
*Assistant Examiner* — Richard M Rump
(74) *Attorney, Agent, or Firm* — Knobbe, Martens, Olson & Bear, LLP

(57) ABSTRACT

Systems and methods for the extraction of carbon nanotubes (CNTs) by continuous and/or batch processing are disclosed. Generally, a carbon nanotube material including carbon nanotubes (CNTs), carbon nanoparticles (CNPs), and carboxylated carbon (CC) is provided and agitated to produce a well-dispersed mixture. The well-dispersed mixture can be allowed to stand in a vessel having a lower end and an upper end. In some cases, the CNPs settle at the lower end. In some cases, at least some of the CNTs and CC are disposed at the upper end and can be removed in a dispersion, which can be pH adjusted and/or filtered to extract the CNTs from the CC.

21 Claims, 22 Drawing Sheets

U.S. PATENT DOCUMENTS

| | | | |
|---|---|---|---|
| 5,457,343 A | 10/1995 | Ajayan et al. | |
| 5,489,477 A | 2/1996 | Ohta et al. | |
| 5,626,812 A | 5/1997 | Ebbesen et al. | |
| 5,641,466 A | 6/1997 | Ebbesen et al. | |
| 5,698,175 A | 12/1997 | Hiura et al. | |
| 5,747,161 A | 5/1998 | Iijima | |
| 5,830,326 A | 11/1998 | Iijima | |
| 5,925,465 A | 7/1999 | Ebbesen et al. | |
| 6,083,624 A | 7/2000 | Hiura | |
| 6,187,823 B1 | 2/2001 | Haddon et al. | |
| 6,331,262 B1 | 12/2001 | Haddon et al. | |
| 6,331,690 B1 | 12/2001 | Yudasaka et al. | |
| 6,368,569 B1 | 4/2002 | Haddon et al. | |
| 6,531,513 B2 | 3/2003 | Haddon et al. | |
| 6,540,972 B1 | 4/2003 | Hiura | |
| 6,641,793 B2 | 11/2003 | Haddon et al. | |
| 6,660,383 B2 | 12/2003 | Toyoda et al. | |
| 6,670,179 B1 | 12/2003 | Mattson et al. | |
| 6,793,737 B2 | 9/2004 | Yount | |
| 7,074,980 B2 | 7/2006 | Prato et al. | |
| 7,090,819 B2 | 8/2006 | Smalley et al. | |
| 7,723,684 B1 | 5/2010 | Haddon et al. | |
| 7,867,468 B1 | 1/2011 | Haddon et al. | |
| 8,052,075 B2 | 11/2011 | Marsh et al. | |
| 8,256,695 B2 | 9/2012 | Marsh et al. | |
| 2002/0094311 A1 | 7/2002 | Smalley et al. | |
| 2004/0071624 A1 | 4/2004 | Tour et al. | |
| 2007/0066171 A1 | 3/2007 | Bystricky et al. | |
| 2008/0069758 A1 | 3/2008 | Campbell | |
| 2009/0285745 A1 | 11/2009 | Ando et al. | |
| 2010/0006152 A1 | 1/2010 | Hatton et al. | |
| 2010/0316557 A1 | 12/2010 | Haddon | |

FOREIGN PATENT DOCUMENTS

| | | |
|---|---|---|
| JP | 2522469 | 8/1996 |
| JP | 2541091 | 10/1996 |
| JP | 2541434 | 10/1996 |
| JP | 2546114 | 10/1996 |
| JP | 2546511 | 10/1996 |
| JP | 2591458 | 3/1997 |
| JP | 2591497 | 3/1997 |
| JP | 2595903 | 4/1997 |
| JP | 2616699 | 6/1997 |
| JP | 2682486 | 11/1997 |
| JP | 2699852 | 11/1997 |
| JP | 2705447 | 1/1998 |
| JP | 2735055 | 1/1998 |
| JP | 2737736 | 4/1998 |
| JP | 2845675 | 1/1999 |
| JP | 2848258 | 1/1999 |
| JP | 3077655 | 8/2000 |
| JP | 3095013 | 10/2000 |
| JP | 3353768 | 12/2002 |
| JP | 3422302 | 6/2003 |
| JP | 3447492 | 9/2003 |
| WO | WO2004/052781 | 7/2004 |

OTHER PUBLICATIONS

B. Gao et al., Fabrication and Electron Field Emission Properties of Carbon Nanotube Films by Electrophoretic Deposition, Advanced Materials, 2001, 13, No. 23, pp. 1770-1773.

H.H. Gommans et al., "Fibers of aligned single-walled carbon nanotubes: Polarized Raman spectroscopy", Journal of Applied Physics, 2000, vol. 88 , No. 5, pp. 2509-2514.

E.T. Thostenson et al., "Carbon nanotube/carbon fiber hybrid multiscale composites," Journal of Applied Physics, 2002, vol. 91, No. 9, pp. 6034-6037.

K. Yamamoto et al., "Orientation of Carbon Nanotubes Using Electrophoresis," Jpn. J. Appl. Phys., 1996, vol. 35, Part 2, No. 7B, pp. L917-L918.

G. Girishkumar et al., "Single-Wall Carbon Nanotube-Based Proton Exchange Membrane Assembly for Hydrogen Fuel Cells", Langmuir 21, 2005, pp. 8487-8494.

G. Girishkumar et al., "Carbon Nanostructures in Portable Fuel Cells: Single-Walled Carbon Nanotube Electrodes for Methanol Oxidation and Oxygen Reduction", J. Phys. Chem. B 108, 2004, pp. 19960-19966.

SES Research, "Nanotubes," http://sesres.com/Nanotubes.asp, Jun. 17, 2009, 4 pages.

Toray Industries, Inc. Torayca Product Line, 2005.

M.W. Marshall et al., "Measurement of functionalized carbon nanotube carboxylic acid groups using a simple chemical process," Carbon 2006, 44, pp. 1137-1141.

E. Bekyarova et al., "Multiscale Carbon Nanotube—Carbon Fiber Reinforcement for Advanced Epoxy Composites", Langmuir 2007, 23, pp. 3970-3974.

Vinod P. Veedu et al., "Multifunctional composites using reinforced laminae with carbon-nanotube forests", Nature Materials 2006, vol. 5, pp. 457-462.

Rahul Sen et al., "Carbon nanotubes by the metallocene route", Chemical Physics Letter 267, 1997, pp. 276-280.

Hui Hu et al., "Influence of the Zeta Potential on the Dispersability and Purification of Single-Walled Carbon Nanotubes", J. Phys. Chem. B 2005, 109, pp. 11520-11524.

Aiping Yu et al., "Application of Centrifugation to the Large-Scale Purification of Electric Are-Produced Single-Walled Carbon Nanotubes", J. Am. Chem. Soc. 2006, 128, pp. 9902-9908.

M.E. Itkis et al., "Purity Evaluation of As-Prepared Single-Walled Carbon Nanotube Soot by Use of Solution-Phase Near-IR Spectroscopy", Nano Letters, 2003, vol. 3, No. 3, pp. 309-314.

Ralph Krupke et al., "Separation of Metallic from Semiconducting Single-Walled Carbon Nanotubes", Science 2003, 301, pp. 344-347.

Jie Tang et al., "Assembly of 1D Nanostructures into Sub-micrometer Diameter Fibrils with Controlled and Variable Length by Dielectrophoresis", Advanced Materials 2003, 15, No. 15, pp. 1352-1355.

Jian Zhang et al., "Efficient Fabrication of Carbon Nanotube Point Electron Sources by Dielectrophoresis," Advanced Materials 2004, 16, No. 14, pp. 1219-1222.

J.K.W. Sandler et al., "Ultra-low electrical percolation threshold in carbon-nanotube-epoxy composites", Polymer 2003, 44, pp. 5893-5899.

Sasha Stankovich et al., "Graphene-based composite materials", Nature, 2006, vol. 442, pp. 282-286.

Aiping Yu et al., "Effect of single-walled carbon nanotube purity on the thermal conductivity of carbon nanotube-based composites", Applied Physics Letters, 2006, 89, pp. 133102-133103.

Xiaoyou Xu et al., "Electrophoretic Analysis and Purification of Fluorescent Single-Walled Carbon Nanotube Fragments", J. Am. Chem. Soc. 2004, vol. 126, No. 40, pp. 12736-12737.

T.W. Chou et al., Textile Structural Composites, Composite Materials Series, vol. 3, Elsevier: Amsterdam, 1988; Russian Edition, Moscow, in 9 pages.

R.W. Cahn et al., Microstructural Design of Fiber Composites; Cambridge University Press: Cambridge, U.K., 1992.

E.T. Thostenson, "Carbon Nanotube-Reinforced Composites: Processing, Characterization and Modeling", Ph.D. Thesis, University of Delaware, 2003.

Haddon et al., "Purification and Separation of Carbon Nanotubes", MRS Bulletin 2004, 29, pp. 252-259.

Itkis, et. al., "Comparison of Analytical Techniques for Purity Evaluation of Single-Walled Carbon Nanotubes", J. Am. Chem. Soc. 2005, 127, pp. 3439-3448.

Zhao, et. al., "Study of the Extinction Coefficients of Single-Walled Carbon Nanotubes and Related Carbon Materials", J. Phys. Chem. B 2004, 108, pp. 8136-8141.

Kimberly A. Worsley et al. Isolation and Identification of Low Molecular Weight Carboxlylated Carbons Derived from Nitric Acid Treatment of Single-Walled Carbon Nanotubes. Carbon 49, 2011, pp. 4982-4986.

Kimberly A. Worsley et al., Functionalization and Dissolution of Nitric Acid Treated Single-Walled Carbon Nanotubes. J. Am. Chem. Soc. 2009, 131, pp. 18153-18158.

Aiping Yu et al., "Gram-Scale Preparation of Surfactant-Free Carboxylic Acid Groups Functionalized, Individual Single-Walled Carbon Nanotubes in Aqueous Solution", Langmuir 2010, 26 (2), pp. 1221-1225.

Noriaki Hamada et al., "New One-Dimensional Conductors: Graphitic Microtubules", Physical Review Letters, vol. 68, No. 10, 1992, pp. 1579-1581.

Zhao, et. al, "Extinction Coefficients and Purity of Single-Walled Carbon Nanotubes", J. Nanosci. Nanotech. 2004, 4, 995-1004.

* cited by examiner

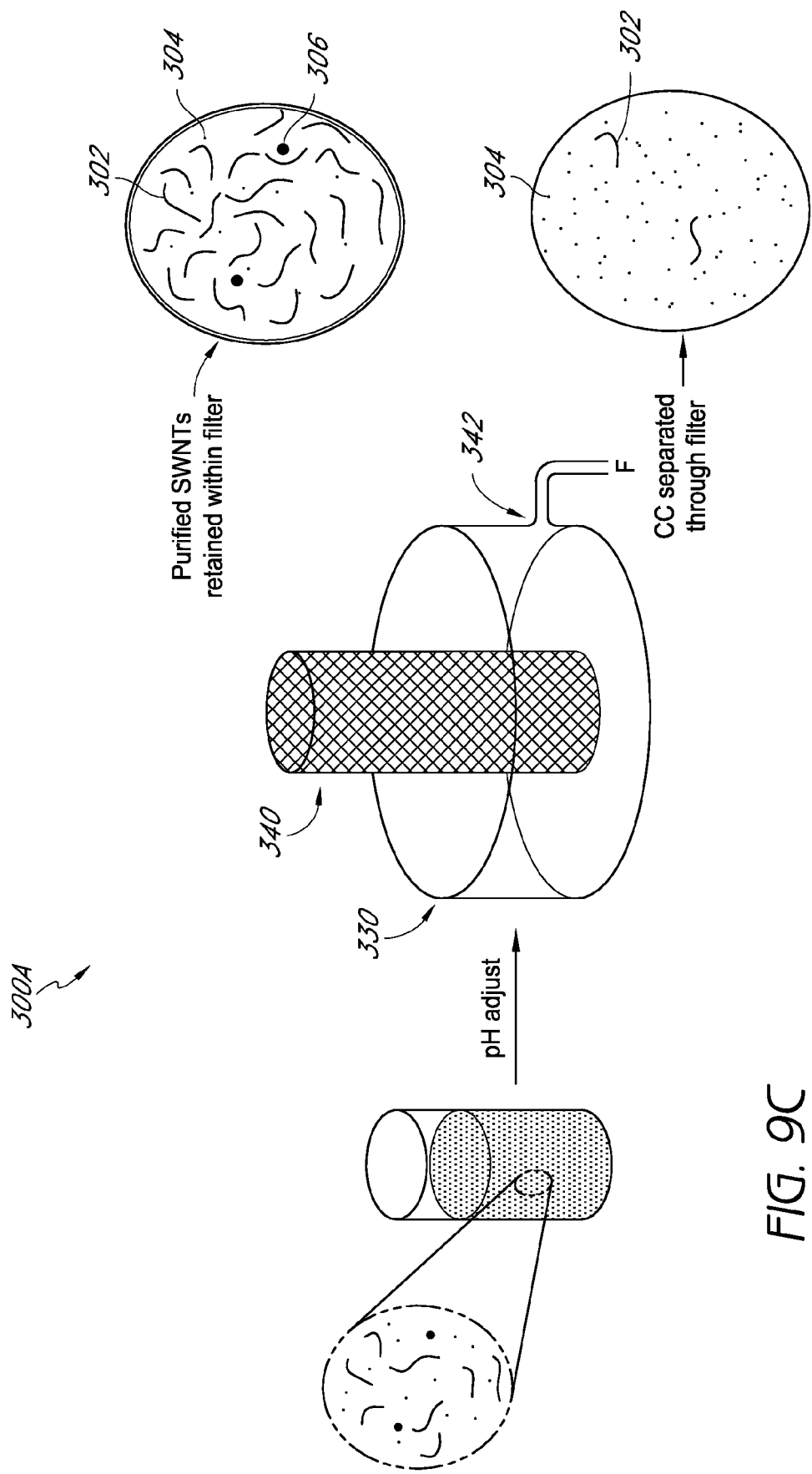

CONTINUOUS EXTRACTION TECHNIQUE FOR THE PURIFICATION OF CARBON NANOMATERIALS

This application is a continuation-in-part of U.S. patent application Ser. No. 12/813,239, filed Jun. 10, 2010, entitled "CONTINUOUS EXTRACTION TECHNIQUE FOR THE PURIFICATION OF CARBON NANOMATERIALS," (which claims the benefit of priority under 35 U.S.C. §119(e) to U.S. Provisional Application No. 61/185,952, filed on Jun. 10, 2009, entitled, "CONTINUOUS EXTRACTION TECHNIQUE FOR THE PURIFICATION OF CARBON NANOMATERIALS," the entirety of which is incorporated herein by reference) and claims priority thereto under 35 U.S.C. §120.

BACKGROUND OF THE INVENTION

1. Field of the Invention

Embodiments of the present disclosure relate to purification of carbon nanomaterials and, in particular, to systems and methods for the removal of impurities from carbon nanotubes.

2. Description of the Related Art

Carbon nanotubes (CNTs) hold significant promise for use in the development of new technologies for national defense and consumer industries. This promise owes in part to the unique combination of nanoscale dimensions and superior chemical and physical properties exhibited by CNTs. Notably, advancements in the carbon nanotube field in the last decade owe much to the progress made in the purification of single-walled carbon nanotubes (SWNTs), as cutting edge technologies benefit significantly from relatively pure materials. As such, efforts to improve the quality of SWNTs are ongoing.

One hindrance to this goal is that the production of SWNTs, and CNTs in general, generate nanotubes that are contaminated with various impurities, such as catalysts, amorphous carbon (AC), and graphitic nanoparticles (GNP). Efficient procedures for the purification of SWNTs have been developed for use in producing small quantities of purified SWNTs for use in laboratories but adapting these techniques to industrial mass production remains problematic. For example, while SWNTs may be treated with nitric acid in order to take catalyst residues into solution and remove them from the SWNTs, the nitric acid also reacts with carbonaceous materials present in the CNTs, producing additional amorphous carbon.

Further purification steps may also be hampered by similarities between the chemical properties of carbon nanotubes and the chemical properties of carbonaceous impurities, as well as the stability of such impurities. In one example, carbon nanoparticle impurities may comprise another form of carbon, such as graphitized carbon, with one or more dangling bonds. As a result of this similarity, it is difficult to chemically attack the impurities without also damaging or destroying the CNTs. Furthermore, some of these impurities have a higher decomposition temperature than nanotubes, limiting the utility of thermal purification techniques. Thus, fabrication of high-purity CNTs necessitates the use of expensive, multi-step purification processes that are ill-adapted and cost prohibitive for industrial scale production.

SUMMARY OF THE INVENTION

In an embodiment, a system for purification of carbon nanotubes is provided. The system comprises a vessel having a first end and a second end and an outlet in a side of the vessel adjacent the first end. The system further comprises a conduit having distal end and a proximal end, wherein the proximal end of the conduit extends through an aperture in the first end of the vessel and is positioned a selected distance from the second end of the vessel. The system additionally comprises a liquid source in fluid communication with the distal end of the conduit and configured to deliver a flow of liquid into the conduit at a flow rate in the range between about 1 to about 10 mL/min. The system also comprises an agitation system configured to stir the liquid within the vessel at a rate in the range between about 20 to 1200 rpm. In certain embodiments, the flow of liquid induces separation of at least a portion of an impurity fraction from a carbon nanotube fraction of a carbon nanotube mixture within the vessel impinged by the flow of liquid. In additional embodiments, the outlet enables at least a portion of a supernatant of the flow of liquid adjacent the first end of the vessel to be extracted from the vessel.

In other embodiments, a method of purifying carbon nanotubes is provided. The method comprises providing a carbon nanotube material comprising a carbon nanotube fraction and at least one impurity fraction. The method also comprises directing a first flow of a water at the carbon nanotube material within a vessel so as to impinge the carbon nanotube material at a first rate in the range between about 1 mL/min to about 4 mL/min, wherein the first flow of water disperses least a portion of a first impurity fraction comprising amorphous carbon within the first flow of water. The method additionally comprises agitating the first flow of water within the vessel at a rate in the range between about 20 to 150 rpm. The method further comprises extracting at least a portion of a supernatant of the first flow of liquid so as to substantially remove the first impurity fraction from the vessel.

In additional embodiments, the method further comprises directing a second flow of a water at the remaining carbon nanotube material within the vessel so as to impinge the remaining carbon nanotube material at a second rate in the range between about 5 mL/min to about 10 mL/min, wherein the second flow of water disperses at least a portion of the second impurity fraction comprising one or more of graphitic nanoparticles and metal containing nanoparticles within the second flow of water. The method may also comprise agitating the second flow of water within the vessel at a rate in the range between about 150 to 1200 rpm. The method may additionally comprise extracting at least a portion of a supernatant of the second flow of liquid so as to substantially remove the second impurity fraction from the vessel.

In some embodiments, a system for extraction of carbon nanotubes includes: a first vessel having an outlet and an agitation system, the first vessel containing a liquid including carbon nanotubes; a flow inducer in fluid communication with the outlet of the first vessel and configured to deliver a flow of liquid into a first conduit; a second vessel having a first end and a second end and an outlet in the side of the second vessel adjacent the first end, the first conduit extending though an aperture in the first end of the second vessel so as to deliver the liquid into the second vessel; a second conduit, in fluid communication with the outlet of the second vessel; and a third vessel having a filter and a pH adjustment system, the second conduit extending though an aperture in the third vessel so as to deliver the liquid from the second vessel to the third vessel; wherein the agitation system agitates the liquid in the first vessel thereby inducing a well-dispersed mixture; wherein the liquid is substantially unagitated in the second vessel for a period of time to induce at least a first impurity to settle to the second end of the second vessel; and wherein the pH adjustment system adjusts the pH of the liquid in the third vessel and the filter filters at least a second impurity from the liquid in the third vessel.

In additional embodiments of the extraction system, the first impurity includes carbon nanoparticles and/or the second impurity includes carboxylated carbon. The liquid can comprise one or more of water, dimethylformamide, tetrahydrofuran, and toluene. In some cases, the agitation system includes a bath sonicator and/or the agitation system agitates the liquid for about 1 to 2 hours. Generally, the aspect ratio of the second vessel ranges between about 1 to 1000. In some cases, the liquid is substantially unagitated in the second vessel for about 6 to 24 hours. Some embodiments also include a monitoring system capable of measuring the amount of carbon nanoparticles in the liquid being provided to the third vessel. In some cases, the pH adjustment system adjusts the pH of the liquid to between about 8 to 9 and/or includes adding NaOH. In some arrangements, the filter includes a nylon mesh bag.

Generally, the carbon nanotubes comprise at least one of single-walled carbon nanotubes (SWNTs), double-walled carbon nanotubes (DWNTs), few-walled carbon nanotubes (FWNTs), and multi-walled carbon nanotubes (MWNTs). Further, the carbon nanotubes can be chemically decorated on at least one of their sidewalls and end caps. In some cases, the carbon nanotubes comprise carboxylic acid-functionalized carbon nanotubes, poly(ethylene glycol) tetrahydrofurfuryl ether functionalized carbon nanotubes (PEG-THFF-SWNTs), octadecylamine functionalized carbon nanotubes (ODA-SWNTs), and polyaminobenzene sulfonic acid functionalized carbon nanotubes (PABS-SWNTs).

In some embodiments, a method of extracting carbon nanotubes includes: providing a carbon nanotube material comprising carbon nanotubes, carbon nanoparticles, and carboxylated carbon; agitating the carbon nanotube material; standing the carbon nanotube material in an elongate vessel having a lower end and an upper end, the carbon nanotube material being is substantially unagitated so as to induce at least a portion the carbon nanoparticles settle to the lower end; removing a dispersion including at least a portion of the carbon nanotubes and carboxylated carbon disposed at or near the upper end; adjusting the pH of the dispersion and; separating at least some of the carbon nanotubes from at least some of the carboxylated carbon in the dispersion.

In further embodiments of the method, agitating occurs for a period of between about 1 to 2 hours to produce a well-dispersed mixture, standing occurs for a period of between about 12 to 36 hours, adjusting the pH includes adjusting the pH to between about 8 to 9, and separating occurs by use of a filter. In some arrangements of the method, the carbon nanotube material includes at least one of single-walled carbon nanotubes (SWNTs), double-walled carbon nanotubes (DWNTs), few-walled carbon nanotubes (FWNTs), and multi-walled carbon nanotubes (MWNTs). In some cases of the method, the carbon nanotubes are chemically decorated on at least one of their sidewalls and end caps. In some embodiments of the method, the carbon nanotubes comprise carboxylic acid functionalized carbon nanotubes, poly(ethylene glycol) tetrahydrofurfuryl ether functionalized carbon nanotubes (PEG-THFF-SWNTs), octadecylamine functionalized carbon nanotubes (ODA-SWNTs), and polyaminobenzene sulfonic acid functionalized carbon nanotubes (PABS-SWNTs).

BRIEF DESCRIPTION OF THE DRAWINGS

FIGS. 9A-9D illustrate embodiments of a non-continuous system similar to the continuous system described in FIGS. 8A-8B;

DETAILED DESCRIPTION

Embodiments of the present disclosure describe systems and methods for the purification of carbon nanotubes (CNTs) by continuous liquid extraction. Carbon nanotubes are introduced to a flow of liquid that enables the separation of CNTs from impurities, in certain embodiments, due to differences in the dispersibility of the CNTs and the impurities within the liquid. Examples of such impurities may include, but are not limited to, one or more of amorphous carbon, graphitic nanoparticles, metal containing nanoparticles, carboxylated carbonaceous fragments, and graphitic fragments. In further embodiments, continuous extraction process may be performed in one or more stages, where one or more of extraction parameters may be varied between the stages of the continuous extraction process in order to effect removal of selected impurities from the CNTs. The extraction parameters that are varied may include, but are not limited to, the extraction liquid, the flow rate of the extraction liquid, the agitation of the liquid, the temperature of the liquid, and the pH of the liquid, depending on the impurity to be removed from the CNTs.

Beneficially, the continuous liquid extraction process yields highly purified CNTs while also maintaining high efficiency. In one example, the efficiency of the continuous extraction process, as measured by its purification recovery factor (PRF), a measure of the fractional quantity of the carbon nanotube product which is recovered after purification, is on the order of about 60-70%. In another example, the carbonaceous relative purity (RP) of carbon nanotubes purified by the continuous extraction process, as measured by near infrared (NIR) spectroscopy, is found to increase over two fold, from about 49% in the starting material to RP greater than about 100%, after purification.

The continuous liquid extraction process is also highly adaptable. In one aspect, the process may be employed with any type of carbon nanotubes, including, but not limited to, single-walled carbon nanotubes (SWNTs), double-walled carbon nanotubes (DWNTs), few-walled carbon nanotubes (FWNTs), and multi-walled carbon nanotubes (MWNTs). In another aspect, the continuous extraction process may be scaled from the laboratory to the industrial scale, with relatively low cost and complexity, in order to provide a selected output of highly pure CNTs. In a further aspect, the process may be used to separate CNTs from one another. These and other advantages are discussed in detail below.

Figure 1A:
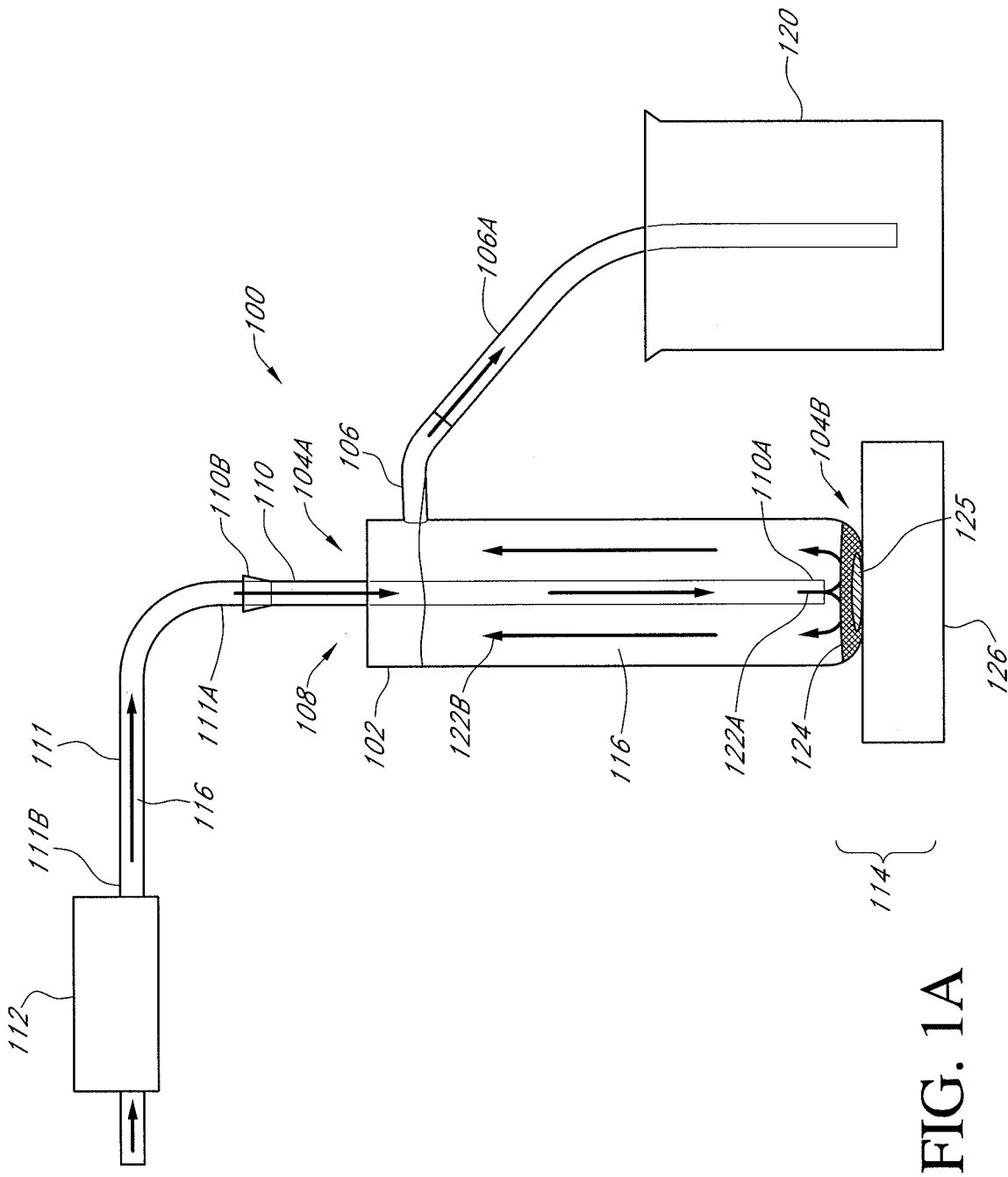
FIGS. 1A-1C schematically illustrate embodiments of a system for continuous extraction purification of carbon nanomaterials; (1A) purification system ready for operation; (1B) extraction of impurity fraction from CNT fraction; (1C) extraction of CNT fraction from impurity fraction.
Figure 1B:
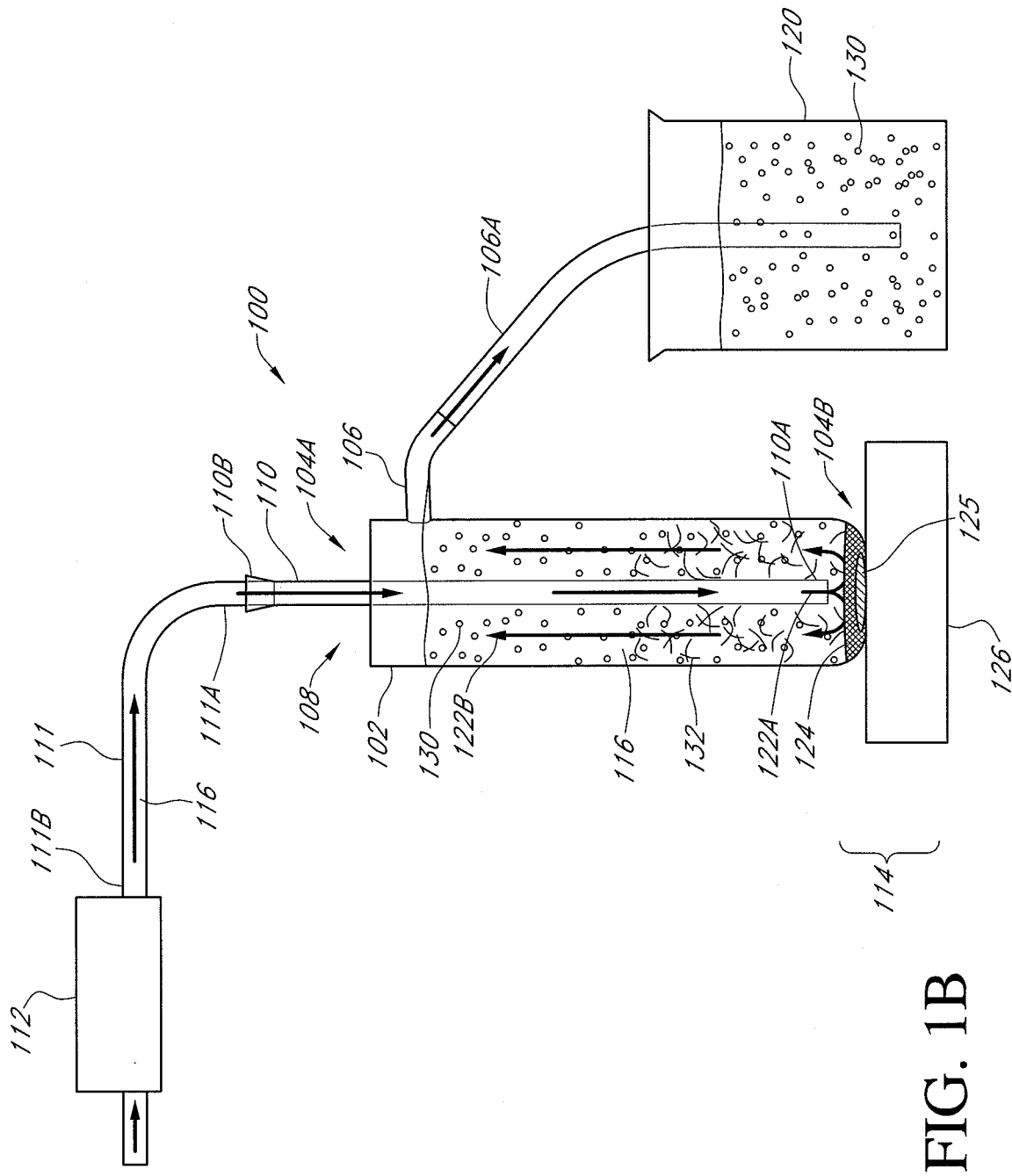
Figure 1C:
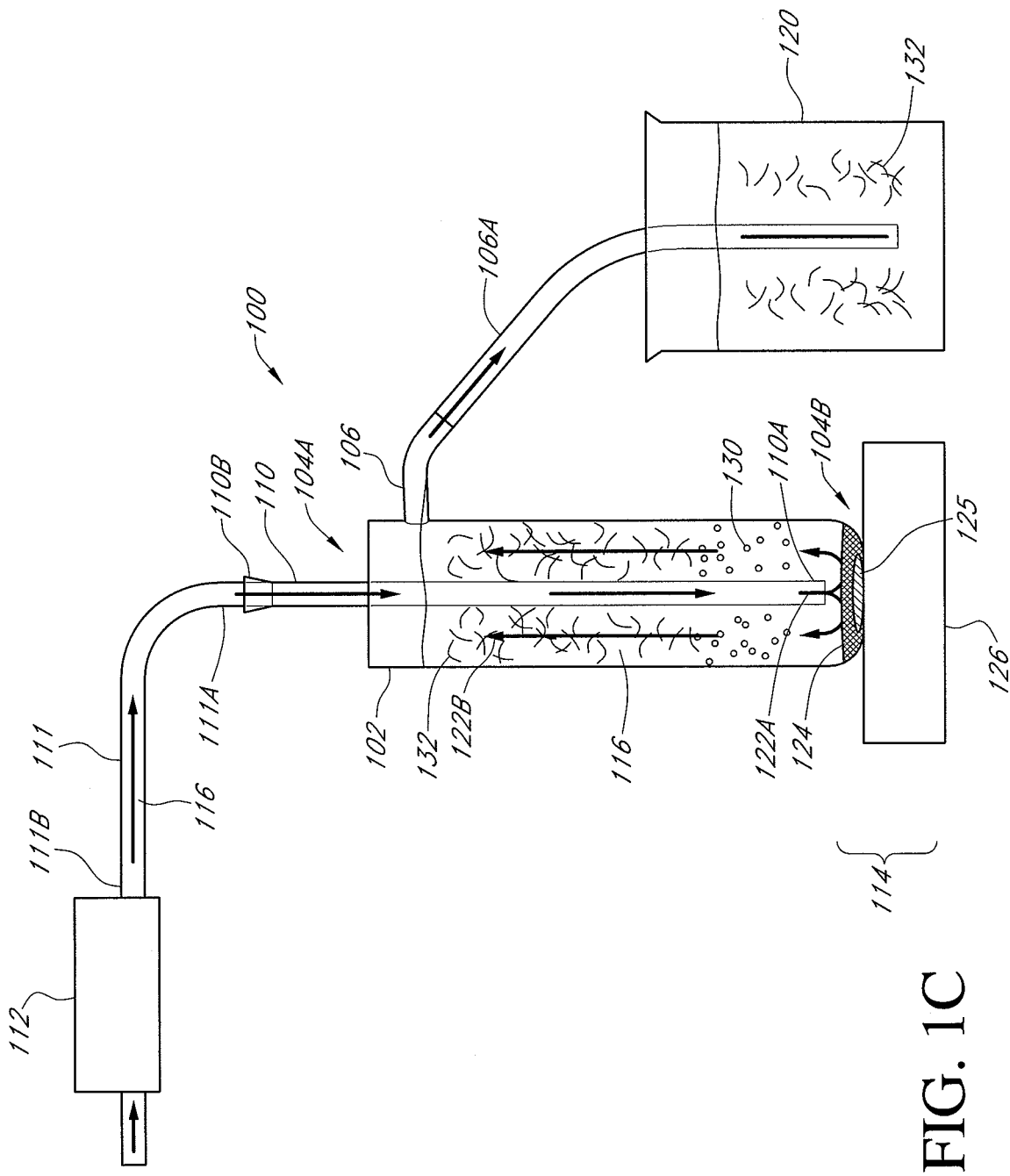

FIGS. 1A-1C illustrate embodiments of a continuous liquid extraction purification system 100 for use in purifying carbon nanotubes. The purification system 100 may comprise a vessel 102, a conduit 110, a liquid flow source 112, a drip line 111, and an agitation system 114. As described in detail below, the drip line 111 may be in fluid communication with the liquid flow source 112. Liquid flow from the liquid flow source 112 may enter the drip line 111 through an inlet 111B of the drip line 111, travel through the drip line 111, and emerge from an outlet 111A of the drip line 111, where it is introduced into the vessel 102 (e.g., dropwise) via the conduit 110 and impinges a carbon nanotube starting material 124 placed within the vessel 102.

The flow of liquid, optionally in conjunction with agitation provided by the agitation system 114, may separate at least one impurity fraction from a carbon nanotube fraction contained within a carbon nanotube starting material contained within the vessel 102. After separation, either the impurity fraction or the carbon nanotube fraction may be extracted from the vessel 102, depending on their relative dispersibility, providing separation of impurities from the carbon nanotubes.

The vessel 102 may comprise a generally elongate body having a first end 104A and a second end 104B. In one embodiment, the vessel 102 may be approximately cylindrical with a diameter that ranges between about 1 to 10 in. and a height that ranges between about 5 to 100 in. In one non-limiting example, the diameter of the vessel 102 may range between about 2 to 6 inches and the height of the vessel 102 may range between about 6 to 25 inches. In other embodiments, the ratio of the height of the vessel to its diameter (i.e., aspect ratio) 102 may range from approximately 1 to 1000, for example, about 1 to 12.

The vessel 102 may further comprise an outlet 106 in fluid communication with a collection chamber 120. The outlet 106, may enable controlled extraction of liquid from the vessel 102 into the collection chamber 120. Extraction may be facilitated by an extension tube 106A in fluid communication with the outlet 106 and positioned so as to deliver extracted liquid into the collection chamber 120. In further embodiments, the extension tube 106A may be a portion of the outlet 106. In one embodiment, the outlet 106 may be positioned adjacent the first end 104A of the vessel 102. In certain embodiments, the outlet 106 may be positioned at a distance that is about 5% of the vessel's height away from the first end 104A of the vessel 102. In alternative embodiments, the outlet 106 may be positioned at a distance that is about 1 in. from the second end 104B of the vessel 102. Liquids removed from the vessel 102 via the outlet 106 may comprise one or more types of impurities, carbon nanotubes, and combinations thereof. In certain embodiments, the liquids collected within the collection chamber 120 may be subjected to analysis and/or disposal.

The vessel 102 may additionally comprise an opening 108 at about its first end 104A that is configured to receive the conduit 110. The conduit 110 may comprise an elongate tube having a proximal end 110A and a distal end 110B. For example, in one embodiment, the conduit 110 may comprise a substantially freestanding eductor tube, but with the end 110B enlarged as described below. The conduit 110 may be further positioned within the vessel 102 such that it extends between the first and second ends 104A, 104B of the vessel 102. The proximal end 110A of the conduit 110 may be positioned at a selected distance adjacent to the second end 104B of the vessel 102 in order to permit operation of the agitation system 114 without interference. In another embodiment, the proximal end 110A of the conduit 110 may be positioned at a distance ranging between about 0.1 to 2 in from the second end 104B of the vessel 102. The length of the conduit 110 may be varied, as necessary, in order to achieve a desired position within the vessel 102, such as adjacent the second end 104B of the vessel 102, while the diameter of the conduit may be in the range between about 0.1 to 5 in.

In certain embodiments, the drip line 111 may be physically separate from the conduit 110. For example, the drip line 111 may be arranged so that flow from outlet 111A drops into the distal end 110B of the conduit 110. For at least this reason the distal end 110B of the conduit 110 may be expanded to enable at least a portion of the outlet 111A of the drip line 111 to fit inside or to be positioned adjacent to the distal end 110B of the conduit 110 with adequate clearance.

The agitation system 114, in one embodiment, may comprise a stirring system. In further embodiments, the agitation system 114 may comprise a magnetic stirring system such as a magnetic stirring bar 125 and a base 126 housing a rotating magnet. In an embodiment, the stirring rate provided by the agitation system 114 may range between about 5 to about 1200 rpm. In other embodiments, the stirring rate provided by the agitation system 114 may range between about 100 to about 500 rpm. In further embodiments, the stirring rate provided by the agitation system 114 may range between about 20 to about 150 rpm.

The distal end 110B of the conduit may be in fluid communication with the liquid flow source 112. In one embodiment, the liquid flow source 112 may comprise a peristaltic pump, gravity flow, or other type of liquid flow control device. The liquid flow source 112 may be configured to provide liquid flow at a rate in the range between about 0.1 to about 1000 mL/min. For example, the liquid flow source 112 may be configured to provide liquid flow in the range between about 0.1 to 1000 mL/min. In further embodiments, liquid flow may be provided in the range between about 1 to 100 ml/min. In additional embodiments, liquid flow may be provided in the range between about 1 ml/min to about 10 ml/min.

Figure 2:
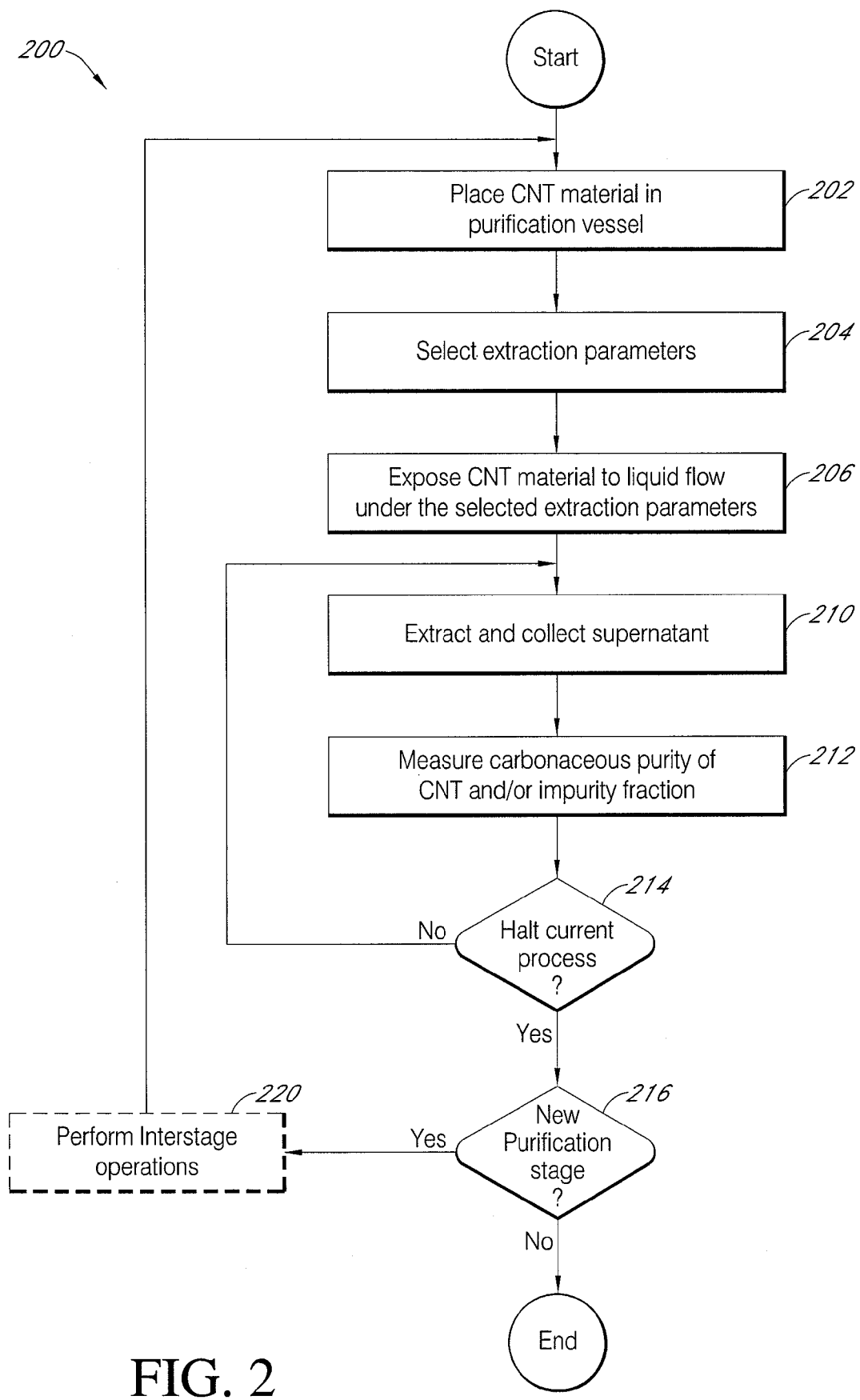
FIG. 2 is a flow diagram of one embodiment of a continuous extraction purification process employing the system of FIGS. 1A-1C.

One embodiment of a continuous liquid extraction purification process 200 is illustrated in FIG. 2, in conjunction with FIGS. 1A-1C. In certain embodiments, the process 200 may be performed in order to separate CNTs from non-CNT impurities. In alternative embodiments, the process 200 may be performed to separate a selected type of CNT from other CNTs, where the type of CNT may refer one or more of the configuration (e.g., SWNTs, DWNTs, FWNTs, MWNTs, chirality), the conductivity (e.g., metallic or semiconducting), or the geometry (e.g., diameter, length) of the CNT. In further embodiments, the process 200 may be configured to purify a selected type of CNT from both non-CNT impurities and other types of CNTs. It may be understood that in alternative embodiments, the process 200 of FIG. 2 may contain greater or fewer operations and may be performed in any order, without limiting the scope of the disclosed embodiments.

In block 202, a CNT starting material 124 may be placed within the purification vessel 102 (FIG. 1A). For example, the CNT starting material 124 may be placed adjacent the second end 104B of the purification vessel 102. It may be understood that the CNT starting material 124 may include CNT materials that have previously undergone continuous liquid extraction purification.

In one embodiment, the CNT starting material 124 may comprise a CNT fraction and one or more impurity fractions. The CNT fraction may comprise one or more types of carbon nanotubes, while the impurity fraction may comprise one or more materials to be removed from the CNT fraction. Examples of impurity fractions may include, but are not limited to, one or more of metal catalysts, amorphous carbon, graphitic nanoparticles, metal containing nanoparticles, carboxylated carbonaceous fragments, and graphitic fragments. In alternative embodiments, the starting material 124 may comprise CNTs alone.

The CNT starting material 124 may also comprise CNTs that are in an as-prepared state (AP-CNTs), a pre-processed CNTs, and combinations thereof. As-prepared CNTs may comprise CNTs that are substantially as-manufactured, while pre-processed CNTs may comprise CNTs that have undergone one or more treatments (e.g., physical, chemical, electro-magnetic, and the like) prior to placement within the system 100.

In one embodiment, pre-processed CNTs may include nitric acid treated CNTs, also referred to interchangeably herein as COOH-functionalized CNTs, owing to functionalization of the CNTs with COOH— groups after nitric acid treatment. For example, pre-processed SWNTs may be formed by refluxing as-prepared SWNTs in an amount in the range between about 10 mg to 1000 g in nitric acid in an amount in the range between about 50 mL to 100 L and in a concentration in a range between about 2M to 16M for a time in the range between about 10 min to 96 hours at a temperature in the range between about 120° C. to 140° C.

In another embodiment, pre-processed CNTs may include CNTs that are chemically decorated. For example, CNTs may be chemically decorated by a range of chemical functionalities. Such decoration may be beneficial in embodiments of the process 200 designed to separate CNTs from one another.

Chemical decorations may be positioned on at least one of the sidewalls and end caps of the CNTs.

In block 204, the extraction parameters for the process 200 may be selected. The combination of extraction parameters employed in the continuous extraction purification system may be chosen so as to achieve purification of the CNTs in a desired manner. For example, the extraction parameters may be chosen in order to remove one or more selected impurities from the CNT starting material 124. In another embodiment, the extraction parameters may be chosen in order to separate one or more selected CNTs from the CNT starting material 124.

The extraction parameters may include, but are not limited to, the extraction liquid, the flow rate of the extraction liquid, the agitation of the liquid, the pH of the liquid, and the liquid temperature. In one embodiment, the liquid may include, but is not limited to, water and dimethylformamide. In a further embodiment, the pH of the liquid within the purification vessel 102 may be in the range between about 0 to about 13. In another embodiment, the liquid flow rate may be in the range between about 0.1 mL/min to about 1000 mL/min. In an additional embodiment, the agitation rate may be in the range between about 5 rpm to about 1200 rpm.

In one embodiment, the selected impurity may be amorphous carbon. The extraction parameters may include, but are not limited to, liquid selection, flow rate, and stir rate. For example, in an embodiment, water may be selected as the liquid. In another embodiment, flow rates may selected within the range between about 1 mL/min to about 4 mL/min. In a further embodiment, stirring rates may be selected within the range between about 20 rpm to about 150 rpm.

In another embodiment, the selected impurity may be graphitic and/or metal containing nanoparticles. The extraction parameters may include, but are not limited to, liquid selection, flow rate, and stir rate. For example, in an embodiment, water may be selected as the liquid. In further embodiments, flow rates may be in the range between about 5 mL/min to about 10 ml/min. In additional embodiments, stirring rates may be selected in the range between about 150 rpm to about 12000 rpm.

In block 206, the CNT starting material 124 within the vessel 102 may be introduced to a flow of liquid 116, for purification, as also illustrated in FIG. 1A. The liquid 116 may flow from the liquid flow source 112, through the drip line 111 and conduit 110, and emerge from the proximal end 110A of the conduit 110 at about the second end 104B of the vessel 102. For clarity, the flow of liquid emerging from about the proximal end 110 of the conduit is illustrated as liquid flow 122A. With the second end 104B of the conduit 110 positioned adjacent the CNT starting material 124, the liquid flow 122A emerging from the conduit 110 may be directed towards the CNT starting material 124.

In certain embodiments, the agitation system 114, such as magnetic stirrer 125, may also be active, agitating the CNT starting material 124 and the liquid 116 as it emerges from the proximal end 110A of the conduit. Beneficially, the mechanical agitation provided by the agitation system 114 may assist in debundling the CNTs within the CNT fraction from one another, as well as debundling impurities from the CNTs.

The liquid flow 122A, after flowing adjacent and/or through the CNT starting material 124, may be redirected towards the first end 104A of the vessel 102 by the walls of the vessel (the redirected flow of liquid 122A is indicated as liquid flow 122B for clarity). In one embodiment, the liquid flow 122B may be directed upwards, against gravity.

Due to the difference in dispersibility between a CNT fraction 132 and one or more selected impurity fractions 130, the flow of liquid 122A adjacent and/or through the CNT starting material 124 may separate at least a portion the impurity fractions 130 from the CNT fraction 132. In one embodiment, the impurity fraction 130 may dissolve within the flow of liquid. In another embodiment, the impurity fraction 130 or the CNT fraction 132 may be mechanically transported by the flow of liquid.

In one embodiment, as illustrated in FIG. 1B, the flow of liquid 122B may transport at least a portion of the impurity fractions 130 towards the first end 104A of the vessel 102. In block 210, at least a portion of the impurity fractions 130 may be extracted from the vessel 102 through the outlet 106 at the first end 104A of the vessel 102 with the supernatant liquid. The impurity fractions 130 and supernatant may be further collected within the collection chamber 120 leaving at least a portion of the impurity fraction 130 within the vessel 102.

In an alternative embodiment, illustrated in FIG. 1C, the flow of liquid 122B may transport at least a portion of the CNT fraction 132 towards the first end 104A of the vessel 102. At the first end 104A of the vessel 102, at least a portion of the CNT fraction 132 may be extracted from the vessel 102 with the supernatant liquid (block 210). The CNT fraction 132 and supernatant liquid may be collected within the collection chamber 120, leaving at least a portion of the CNT fraction 132 within the vessel 102.

In decision block 214, a determination may be made as to whether the current purification process is to be halted. The current purification process may include selected levels of purification parameters, while a new purification process may include at least one purification parameter which is different than those of the current purification process. In order to make this determination, the carbonaceous purity of the CNT and/or impurity fractions 130, 132 may be measured in block 212. If a determination to continue the process 200 is made in decision block 214 (e.g., a selected level of purification is not achieved in at least one of the CNT and impurity fractions 132, 130, as discussed below), the process returns to block 210, where extraction and collection of the supernatant liquid within the purification vessel is continued. The process loop of blocks 210-214 may be repeated until a selected level of carbonaceous purity is measured in at least one of the CNT and impurity fractions. If a determination to halt the process is made in decision block 214 (e.g., a selected level of purification is achieved in at least one of the CNT and impurity fractions 132, 130), the process 200 moves to block 216, where a further determination is made whether to begin a new stage of the purification process. If no further purification is to be performed, the process 200 ends.

If another purification stage is determined to be performed in decision block 216, the process may return to block 202, where the CNT fraction 132 becomes the CNT starting material 124 for the subsequent purification stage. In one embodiment, the new stage of the purification process 200 may be performed, starting from block 202, using one or more extraction parameters which are different from the immediately prior purification stage. In this manner, one or more additional impurity fractions not substantially removed under the extraction parameters for the current process, may be removed from the CNT fraction 132. Thus, by performing the process 200 additional times, selecting one or more extraction parameters in block 204 that are different than those previously employed in the process 200, the one or more additional impurity fractions 130 may be removed from the CNT fraction 132, further purifying the CNT fraction 132.

In one embodiment, an individual purification stage and/or the process 200 may be halted upon achievement of a selected value of relative carbonaceous purity of the CNT fraction 132. For example, the selected relative carbonaceous purity may range between about 80 to 180%. In another embodiment, an individual purification stage and/or the process 200 may be halted upon achievement of an asymptotic value of the relative carbonaceous purity of the CNT fraction 132. In a further embodiment, an individual purification stage and/or the process 200 may be halted upon achievement of a relative carbonaceous purity of the impurity fraction 130 approaching the relative carbonaceous purity of the CNT starting material 124. In an additional embodiment, an individual purification stage and/or the process 200 may be halted when the continuous extraction purification process becomes inefficient, for example, as measured by the purification recovery factor of the CNT fraction 132, as discussed below.

In certain embodiments, the method 200 may be performed multiple times, with the extraction parameters being varied so as to remove selected impurities from the carbon nanotube material 124. In further embodiments, one or more purification stages may be performed with at least a portion of the CNT fraction of the carbon nanotube material within the liquid contained within the vessel. The CNT fraction 132 may then be extracted from the vessel 102 for further use. For example, one or more purification stages employing extraction parameters which disperse the CNT fraction 132 may be conducted once the CNT material has been subjected to other purification stages which have removed selected impurities. In this manner, the extracted, purified CNT fraction may possess a carbonaceous purity ranging between about 80 to 180%.

In other embodiments, additional operations to facilitate the purification process 200 may optionally be performed on the CNT fraction 132 in block 220 between stages of the continuous extraction purification process 200 (also referred to as interstage processes). In one embodiment, the CNT fraction 132 may be subjected to ultrasonic agitation. For example, the purification vessel 102 may be placed within an ultrasonic bath and exposed to ultrasonic energy at a frequency in the range between about 10,000 Hz to about 100,000 Hz for a time in the range between about 10 min to about 48 h. This agitation may further assist in debundling the CNTs from one another and separating the CNT fraction 132 from impurity fractions 130, leading to a more stable suspension of CNTs within the liquid 116.

In order to provide the continuous extraction purification system 100 with analytical capabilities, at least one of the sediment within the purification vessel 102 and the supernatant extracted from the vessel 102 may also be monitored at selected times during the purification process by a purification monitoring system. In one embodiment, monitoring may include carbonaceous purity evaluation by one or more of near-infrared-visible (near-IR-Vis) spectroscopy analysis or mid-infrared spectroscopy analysis. As such, the purification monitoring system may comprise one or more of a visible wavelength spectrometer, a near-infrared wavelength spectrometer, and a mid-infrared wavelength spectrometer. Embodiments of such spectroscopy analyses may be found in Haddon, et al., "Purification and Separation of Carbon Nanotubes", *MRS Bulletin* 2004, 29, 252-259; Itkis, et. al., "Comparison of Analytical Techniques for Purity Evaluation of Single-Walled Carbon Nanotubes", *J. Am. Chem. Soc.* 2005, 127, 3439-3448; and Itkis, et al., "Purity Evaluation of As-Prepared Single-Walled Carbon Nanotube Soot by Use of Solution Phase Near-IR Spectroscopy", *Nano Lett.* 2003, 3, 309-314, the entirety of each of which is hereby incorporated by reference.

In the carbonaceous purity analysis, the ratio of the area of a selected absorption feature corresponding to the CNTs after baseline subtraction to the total area under the spectral curve from solution phase near-IR spectra may be monitored. For example, dilute dispersions, having a concentration of analyte of in the range between about 0.001 mg/mL to 0.1 mg/mL, in dimethylformamide (DMF) may be compared with a reference sample on the basis of areal absorbance in the spectral range between about 5000 cm$^{-1}$ to about 17000 cm$^{-1}$. In one embodiment, the reference sample may comprise R2. For example, the spectral range between about 7750 cm$^{-1}$ to about 11750 cm$^{-1}$ covers the $S_{22}$ interband transition of electric arc produced SWNTs. In alternative embodiments, the spectral range between about 8000 cm$^{-1}$ to about 12700 cm$^{-1}$ or about 8500 cm$^{-1}$ to about 13700 cm$^{-1}$ covers laser ablation produced carbon nanotubes under different synthetic parameters. In further embodiments, the spectral range between about 7750 cm$^{-1}$ to about 11750 cm$^{-1}$ or about 8500 to about 13700 cm$^{-1}$ covers amorphous carbon.

Relative purity values higher than 100% correspond to CNT samples with a relative purity higher than that of the reference sample. The efficiency of the purification procedure may be evaluated using the purification recovery factor (PRF), which measures the fraction of the desired product that is recovered after the purification with respect to the amount of product initially present in the starting sample. Assuming that a measure of the absolute carbonaceous purity, P, is available, Equation 1 provides the PRF:

$$PRF=[P(product)/P(starting\ material)] \times Y(\%) \qquad (Eq.\ 1)$$

where Y is the yield of the product after purification. In one embodiment, the yield is given by the weight percentage of carbonaceous material. In certain embodiments, the yield may be corrected for metal content.

When the only available measure of carbonaceous purity is the relative purity, RP, P may be given by P=Z×RP where Z is an unknown factor with a value less than 1. The absolute value of the PRF can be obtained from Equation 2:

$$PRF=[RP_{(product-CNT)}/RP_{(starting\ material-CNT)}] \times Y(\%) \qquad (Eq.\ 2)$$

The relative purity of the materials may be obtained from the ratio of selected absorption features after baseline subtraction and the total area under the spectral curve from solution phase near-IR spectra.

In another embodiment, the rate of material extracted from the vessel 102 in the supernatant can be monitored. In an example, the system 100 illustrated in FIGS. 1A-1C may further comprise a rate monitor capable of measuring the rate of material extracted from the vessel in the supernatant. In one embodiment, the rate monitor may comprise a light emitting diode (LED) and photodetector measurement system. The LED and photodetector may be placed at opposite sides of the purification vessel 102 in order to make rate measurements. For example, the LED and photodetector may be placed at about the first end 104A of the purification vessel 102. Alternatively, a spectroscopic window may be installed within the outlet 106. After calibration, the rate monitor may allow monitoring of the concentration and rate of mass extraction of carbonaceous material on the basis of an extinction coefficient analysis. Additional information regarding the extinction coefficient analysis may be found in Zhao, et. al, "Extinction Coefficients and Purity of Single-Walled Carbon Nanotubes", *J. Nanosci. Nanotech.* 2004, 4, 995-1004 and Zhao, et. al., "Study of the Extinction Coefficients of Single-Walled Carbon Nanotubes and Related Carbon Materials", *J. Phys. Chem. B* 2004, 108, 8136-8141, the entirety of each of which is hereby incorporated by reference.

In a further embodiment, the carbonaceous purity of the extracted material may be monitored by utilizing a 2-color or 3-color LED in combination with the frequency of one LED-photodetector measurement system matching the interband electronic transition of the CNTs, for example, the $S_{22}$ interband electronic transition of SWNTs, and the frequencies of one or two other LED-photodetector measurement systems selected to evaluate the baseline correction such that the purity of the extracted material can be monitored.

In certain embodiments, the carbonaceous purity may be examined continuously. In other embodiments, the carbonaceous purity may be assessed at intervals, for example, in the range between about 1 to about 3 days. Beneficially, once parameters of the process, such as water flow level and stirring rate, are established for a particular process scale, vessel size, and geometry, the time required for the completion of the purification may be established without the need for repeated purity testing.

EXAMPLES

In the following examples, embodiments of the continuous extraction purification process for carbon nanotubes are discussed in greater detail. The examples highlight the high purity CNTs that may be achieved from the purification process, as well as the high efficiency and adaptability of the purification process. It may be understood, however, that these examples are discussed for illustrative purposes and should not be construed to limit the disclosed embodiments.

Example 1

Microscopy Study of Nitric Acid Treated SWNTs Purified by Continuous Extraction Purification Process The ability of the continuous extraction process 200 to remove impurity fractions from a CNT fraction 132 may be observed by microscopy of the CNT starting material 124, as well as those materials remaining within the vessel 102 and collected from the supernatant after different stages of the continuous extraction purification process. For example, FIGS. 3A-3C illustrate Scanning Electron Microscope (SEM) images of embodiments of SWNTs at various stages of the purification process.

A first purification stage was performed using extraction parameters selected to achieve removal of amorphous carbon impurities from a CNT starting material comprising nitric acid treated SWNTs. In one embodiment, the liquid was water, the liquid flow rate during the first stage purification was selected to be about 2.5 mL/min, and the stirring rate was in the range between 20 to 150 rpm. The pH of the water was not adjusted during the course of the purification and was observed to increase from an initial value of about 2 to 4 during the course of purification.

A second purification stage was performed using extraction parameters selected to achieve removal of graphitic and metal containing nanoparticles. Examples of metal containing nanoparticles may include, but are not limited to, encapsulated metal catalysts, Fe, Ni, Co, and Y, or graphitic nanoparticles. In further embodiments, the encapsulated metal catalysts can be emptied, with metal catalyst removed, during prior steps of processing. In an embodiment, the second stage of the continuous extraction process employed a higher liquid flow rate, about 5 to 10 mL/min, and a higher stirring rate, about 150 to 12000 rpm, as compared with the first stage of the extraction process, while the liquid remained water at a pH of about 3 to 7.

Figure 3A:
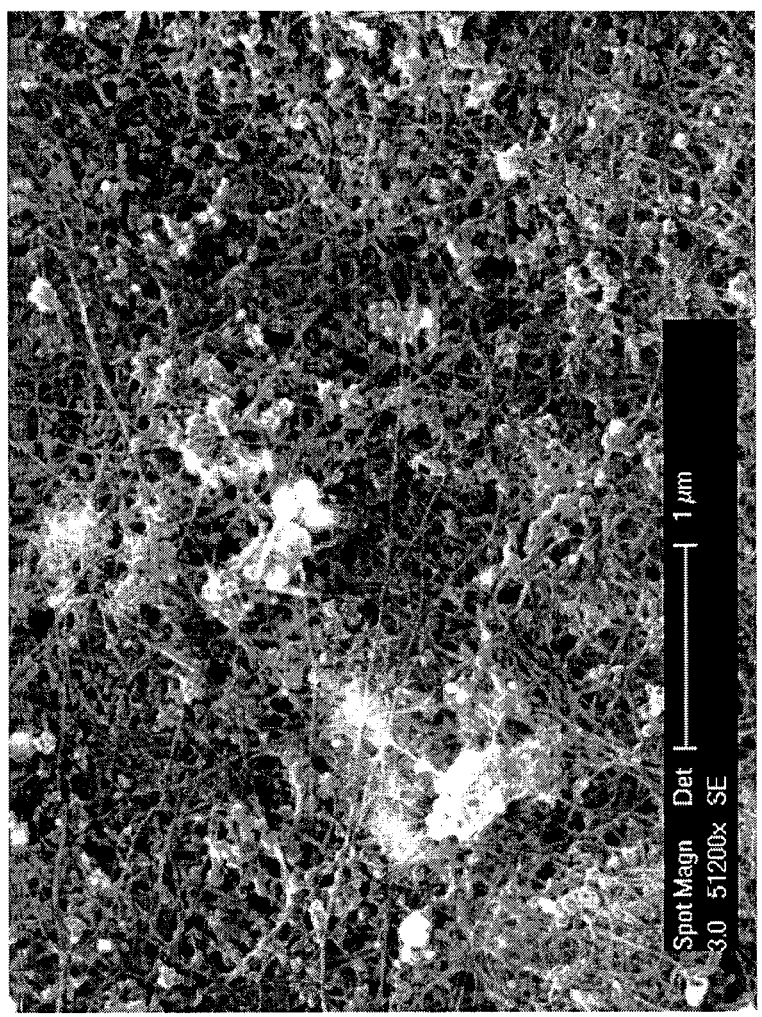
FIGS. 3A-3C are scanning electron microscope (SEM) images of embodiments of SWNTs at various stages of a purification process performed using the system of FIGS. 1A-1C; (3A) pre-purified, SWNTs treated with nitric acid, illustrating embedded catalyst nanoparticles; (3B) CNT fraction after a first stage of continuous extraction purification illustrating substantially purified single walled carbon nanotubes (SWNTs); (3C) amorphous carbonaceous impurity fraction after the first stage of continuous extraction purification.
Figure 3B:
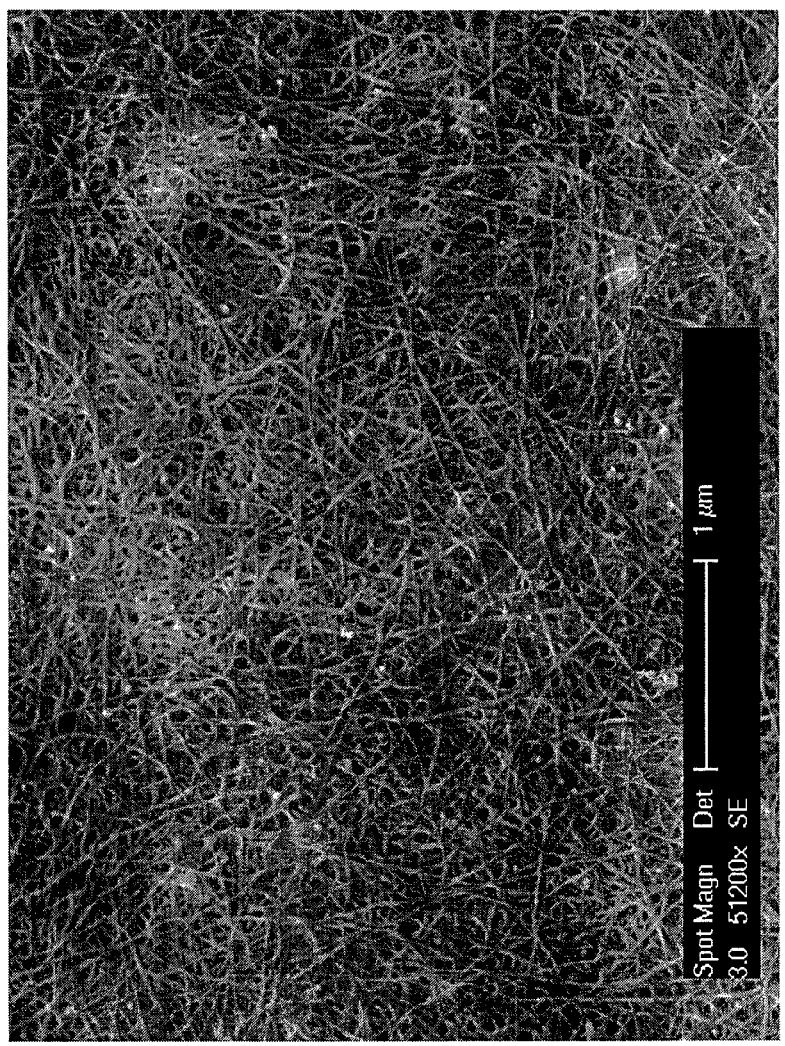
Figure 3C:
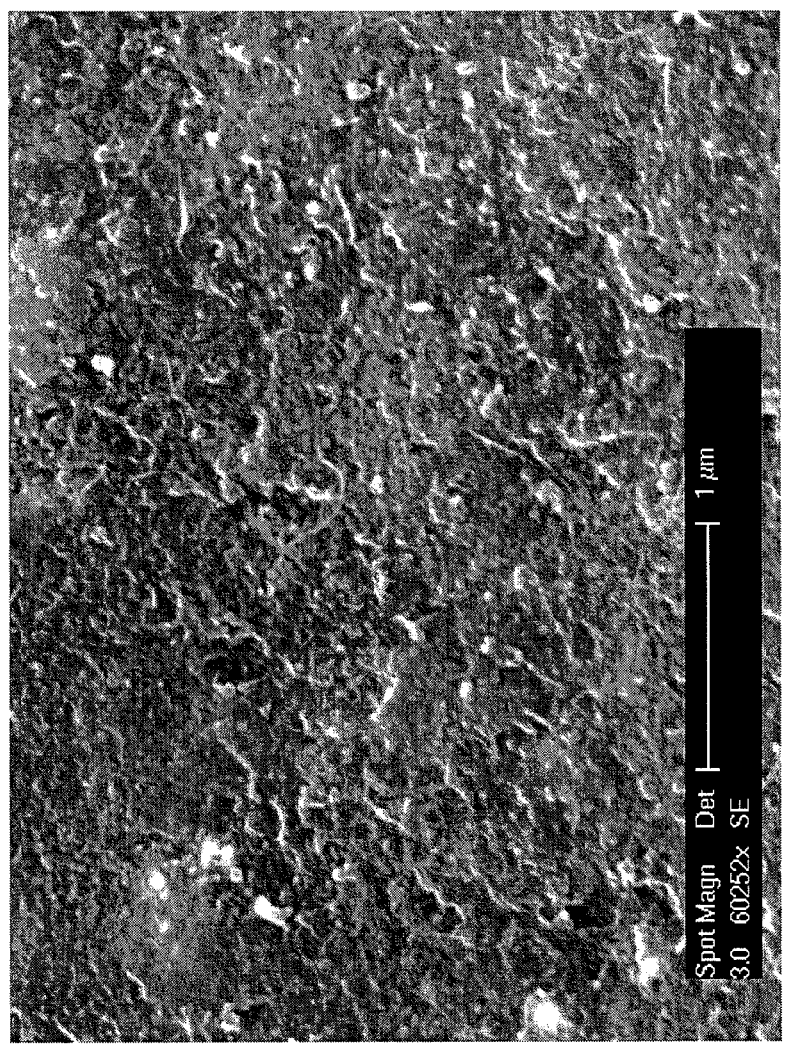

FIGS. 3A-3C are scanning electron microscope (SEM) images of embodiments of SWNTs at various stages of a purification process performed using the system of FIGS. 1A-1C. FIG. 3A illustrates pre-purified SWNTs treated with nitric acid, illustrating embedded catalyst nanoparticles and amorphous impurities. FIG. 3B illustrates the CNT fraction after a first stage of continuous extraction purification, illustrating substantially purified single walled carbon nanotubes (SWNTs). FIG. 3C illustrates amorphous carbonaceous impurities. It may be observed that the CNT material remaining in the vessel 102 appears substantially free from amorphous impurities (FIG. 3B), while extracted fraction is rich in non-CNT carbon material (FIG. 3C).

Example 2

Purification of Nitric Acid Treated SWNTs for Continuous Extraction Purification Process A CNT paste was produced from as-prepared Single Walled Carbon Nanotubes (AP-SWNTs) by nitric acid treatment. The AP-SWNTs were manufactured by Carbon Solutions, Inc. (Riverside, Calif.) through an electric arc-discharge process. The AP-SWNTs possessed a mean length of approximately 3 μm and a mean diameter of about 1.4 nm.

Approximately 50 grams of the AP-SWNTs, having an initial relative carbonaceous purity (RP) of about 49%, were refluxed in about 3 L of approximately 16M nitric acid for about 90 minutes at about 120° C. This operation generated about 34 g of a black pre-processed SWNT material having a relative purity of about 68%.

After cooling the pre-processed SWNT mixture to about room temperature, the SWNT mixture was filtered and washed with distilled water on a filtration membrane to substantially remove excess acid. The resulting wet paste was transferred to an approximately 1 L flask, diluted with approximately 500 mL of distilled water and stirred for about 30 minutes at a speed of about 200 rpm to obtain an approximately homogeneous slurry of the SWNT starting material. The slurry was poured into a purification vessel 102 having a capacity of about 4 L and diluted with distilled water. The resulting mixture was allowed to settle for about 1 hour in order to allow the establishment of a natural concentration gradient within the vessel 102.

The extraction process was started after addition of the slurry to the purification vessel 102. An agitation system 114 comprising a magnetic stirrer was employed to stir the pre-processed SWNT mixture within the vessel 102, and the magnetic stirrer was set to revolve at about 80 rpm. The liquid flow source 112 was further set to deliver a flow of distilled water to the purification vessel 102 at a rate of about 4 mL/min.

Small probe samples, about 10-20 mL, of the material from the top and the bottom of the purification vessel 102 were taken approximately once per 24 hour period. These samples were analyzed with near-IR spectroscopy in order to monitor the relative carbonaceous purity of the purified and extracted fractions, as illustrated in FIGS. 4A-4B.

Figure 4A:
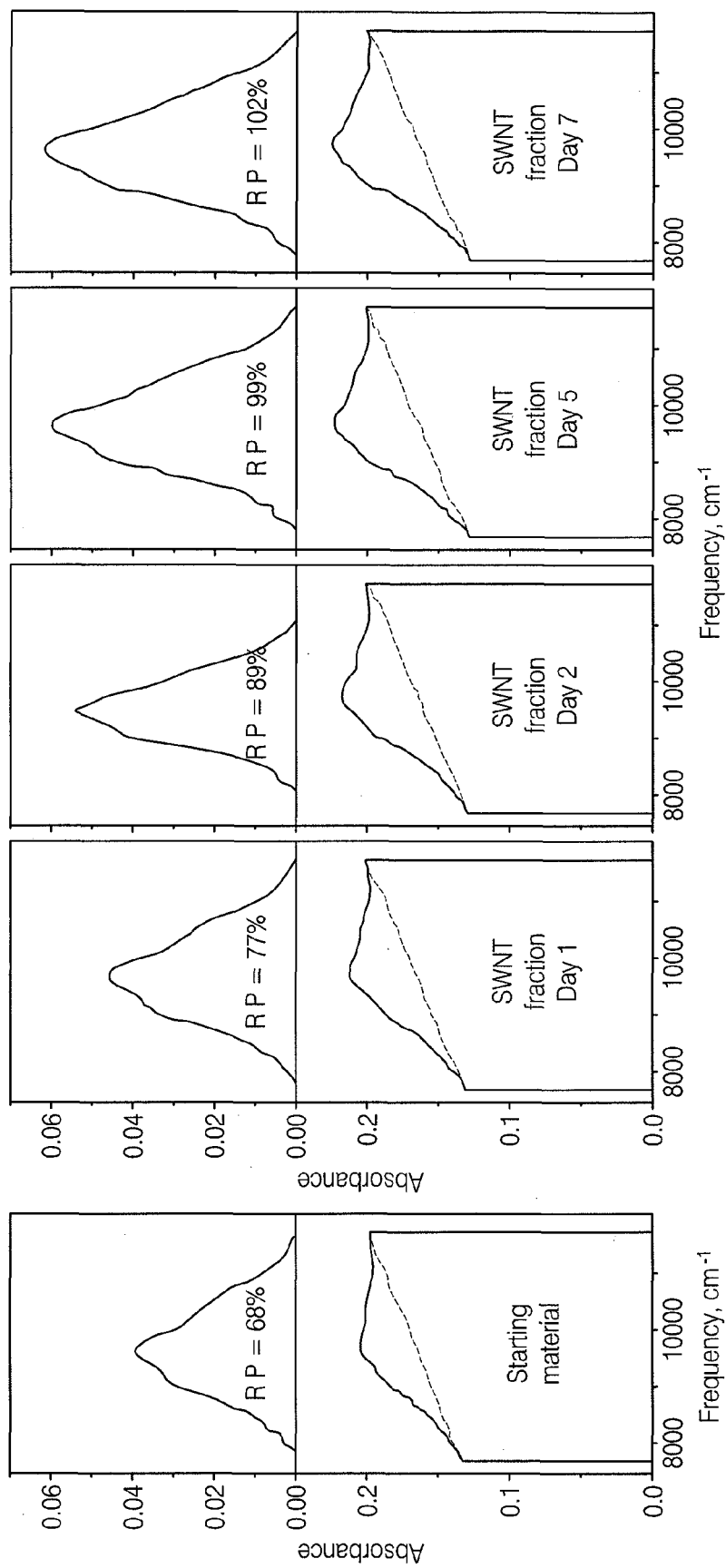
FIGS. 4A-4B are spectra of absorbance as a function of frequency measured using near-IR purity evaluation spectroscopy for embodiments of SWNTs purified using the purification system of FIGS. 1A-1C; (4A) purified SWNT fraction; (4B) extracted impurity fraction.
Figure 4B:
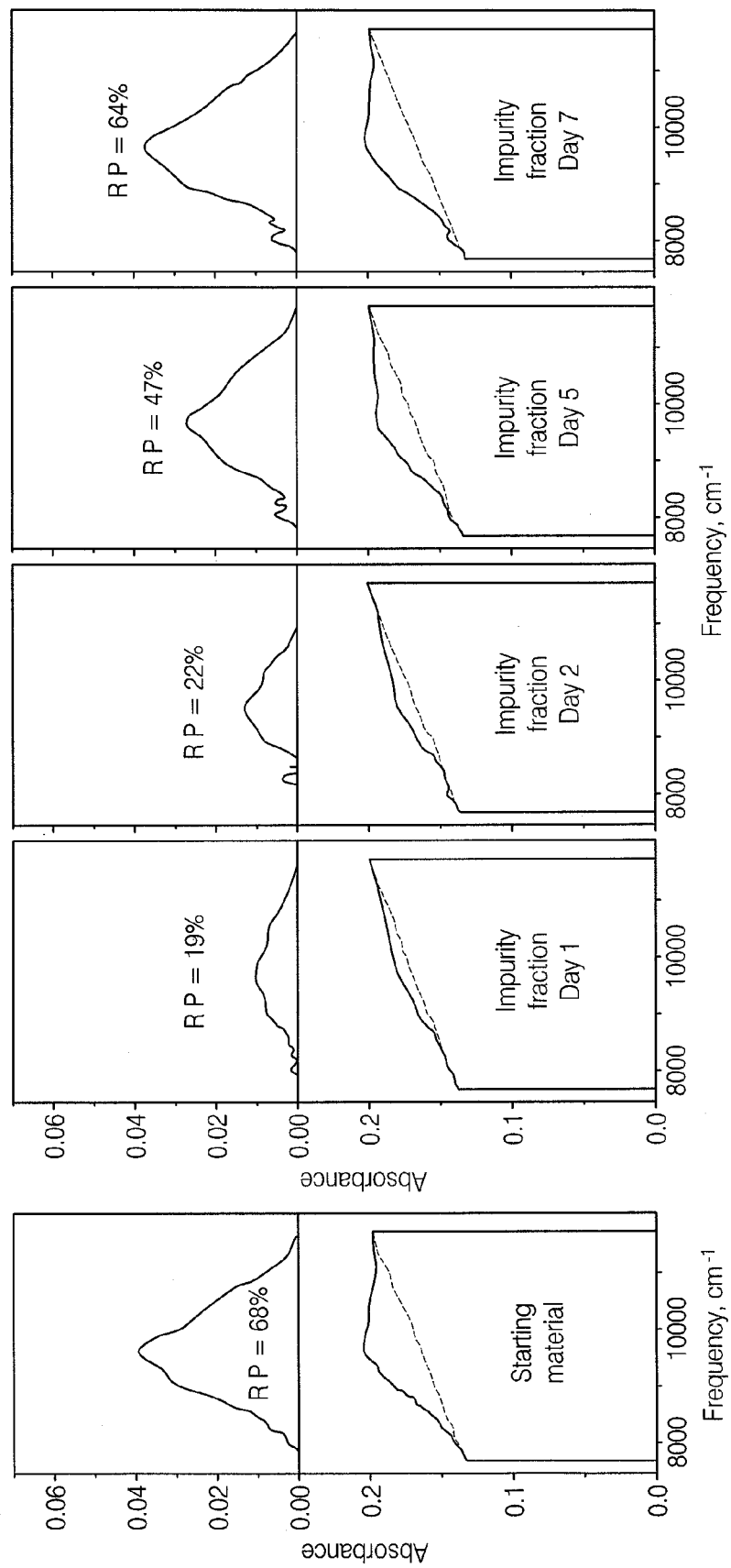
Figure 5:
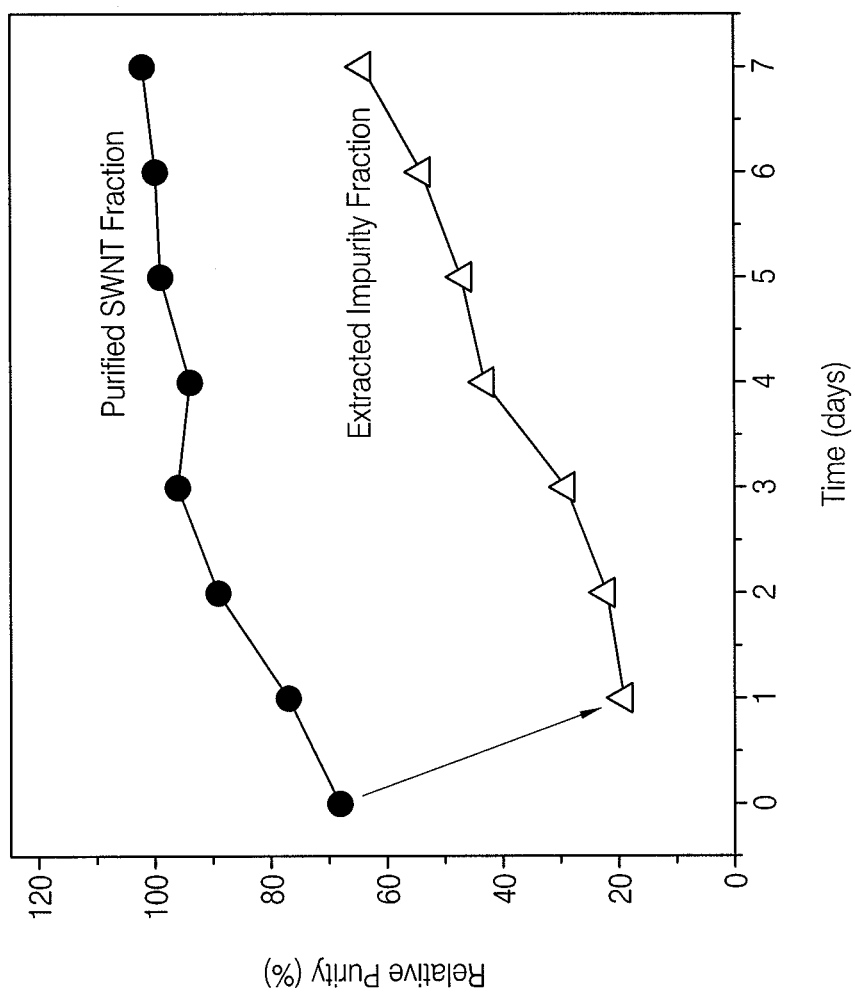
FIG. 5 is a plot of relative purity versus time, illustrating the evolution of the relative purity of a purified fraction of the purified SWNT fraction and the extracted impurity fraction from the carbon nanomaterials undergoing purification in FIGS. 4A-4B.

FIGS. 4A-4B illustrate examples of near-IR spectra measured on samples of the starting SWNT material, as well as the SWNT and impurity fractions after 1, 2, 5, and 7 days. A companion plot presenting the daily evolution of the relative carbonaceous purity during the first stage of purification for both fractions is illustrated in FIG. 5. It may be observed that, over the 7 day period examined, the relative carbonaceous purity of the sediment at the bottom of the purification vessel, the SWNT fraction, increased from about 68% in the initial starting material to about 102% (FIG. 4A). Concurrently, the impurity fraction extracted from the vessel was found to exhibit a relative purity of about 20% after day 1, increasing to about 47% by day 5, and reaching about 64% by day 7 (FIG. 4B).

Figure 6A:
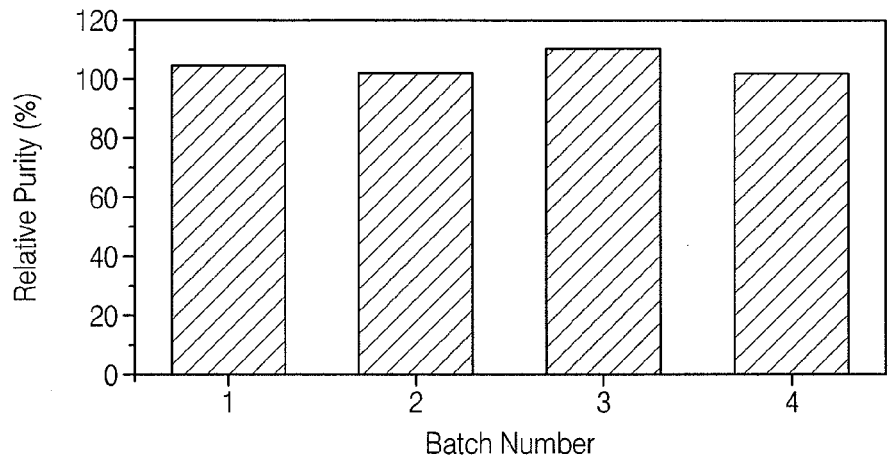
FIGS. 6A-6C illustrate measurements of relative purity (6A), yield (6B), and purification recovery factor (PRF) (6C) for batches of carbon nanotubes purified using the system of FIGS. 1A-1C.
Figure 6B:
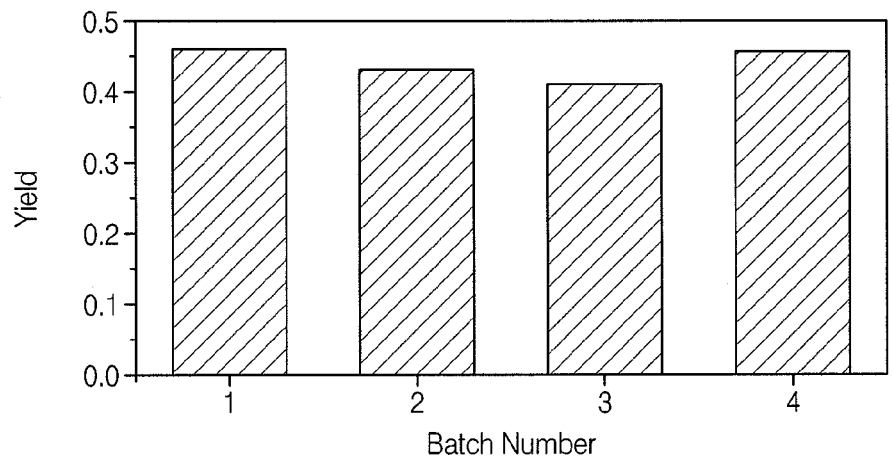
Figure 6C:
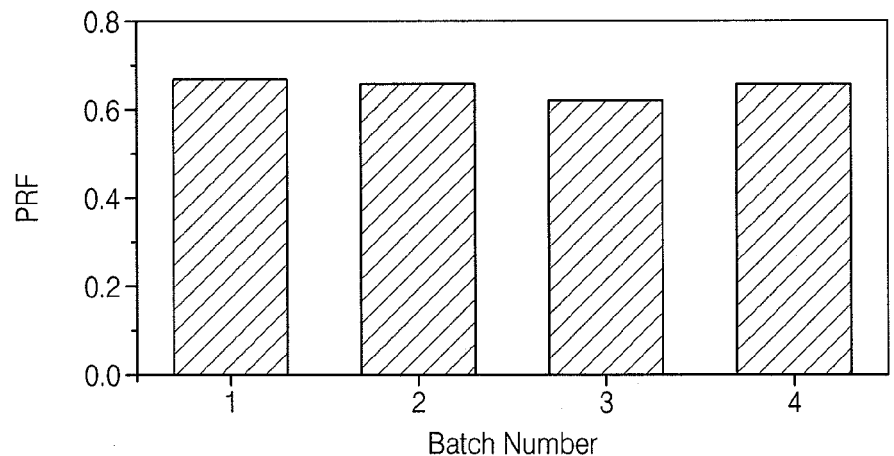

The reproducibility of the continuous extraction process was investigated by performing four different trials to purify approximately 50 g batches of as-processed SWNTs. Table 1 presents measurements and calculated values for mass and relative purity of the starting AP-SWNTs, the pre-purified SWNTs after acid reflux, and the purified SWNTs after continuous extraction purification, as well as the yield and PRF values calculated for the purified SWNTs. FIGS. 6A-6C summarizes the relative carbonaceous purity, yield, and PRF results of results of Table 1 in histogram form.

TABLE 1

Results of purification of four 50 g batches of AP-SWNTs

| | Starting AP-SWNTs | | Acid Reflux | | Continuous Extraction (CE) | | | | |
|---|---|---|---|---|---|---|---|---|---|
| Batch | Mass | Relative purity | Mass | Relative Purity | Time | Final Mass | Final Purity | CE Yield | CE PRF |
| 1 | 50 g | 49% | 33.0 g | 72% | 4 days | 15.3 g | 105% | 0.46 | 0.67 |
| 2 | 50 g | 49% | 35.5 g | 68% | 4 days | 15.6 g | 103% | 0.44 | 0.66 |
| 3 | 50 g | 49% | 35.6 g | 74% | 4 days | 14.8 g | 111% | 0.41 | 0.62 |
| 4 | 50 g | 49% | 36.5 g | 71% | 6 days | 16.8 g | 102% | 0.46 | 0.66 |

As illustrated in Table 1 and FIGS. 6A-6C, the relative carbonaceous purity of the SWNTs in the four batches began at about 49% in the as-processed state and increased to approximately 102-111% in the purified state, a variation of less than about 10%. Furthermore, the yield of the purified SWNTs was approximately 0.41-0.46 and the purification recovery factor (PRF) ranged from about 0.62-0.67, again, demonstrating a variation of approximately 10%. Thus the process has a high reproducibility and can be completely automated.

Figure 7A:
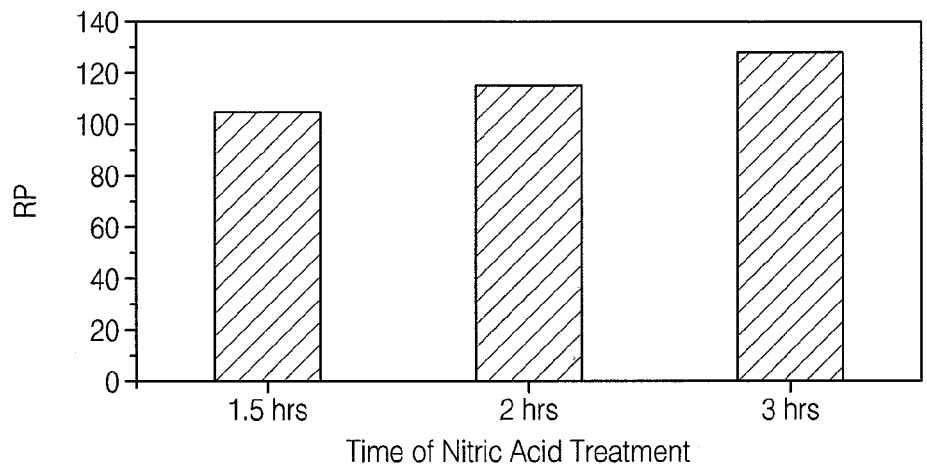
FIGS. 7A-7C illustrate measurements of relative purity (7A), yield of purification (7B), and purification recovery factor (PRF) (7C) as a function of time of nitric acid treatment of carbon nanotubes undergoing purification.
Figure 7B:
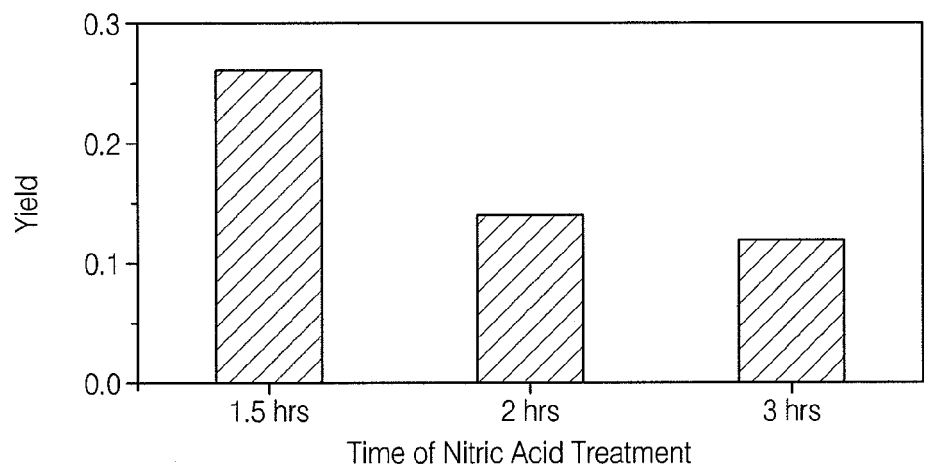
Figure 7C:
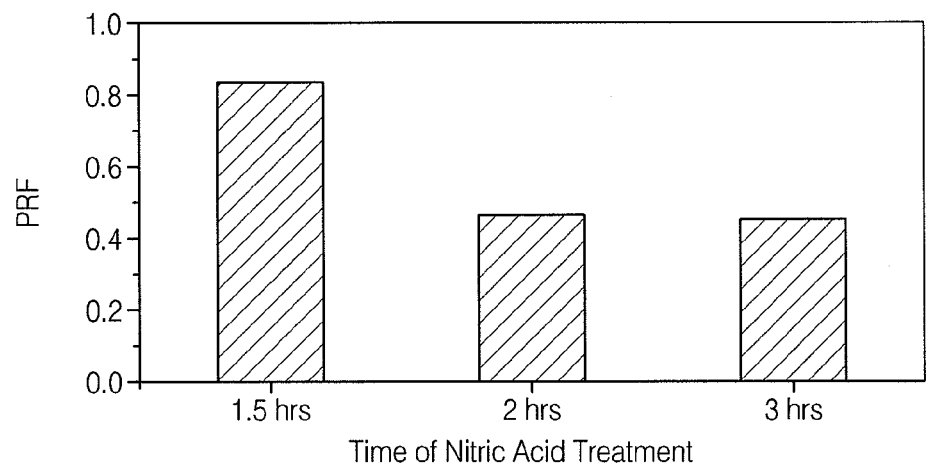

The PRF can be further improved by optimization of the water flow, magnetic stirring rate, pH of the solvent and the apparatus geometry. As shown in Table 1, approximately 4-6 days elapsed in order to complete the purification process. During this time, about 15 to 17 g of purified SWNTs were produced for each batch. As a result of this purification procedure the metal content of the SWNTs was observed to decrease from about 30-35% in the as-prepared state to about 4-7% in the final purified product. For example, as illustrated in FIG. 7, by increasing the time of nitric acid treatment, it is possible to increase carbonaceous purity of the final product from 105 to 128%, although yield of purification and PRF decrease.

Example 3

Purification of Chemically Functionalized SWNT-PEG-THFF Material

SWNT-polyethylene glycol-tetrahydrofurfuryl-ether (SWNT-PEG-THFF) is a typical member of the family of chemically functionalized SWNTs with the chemical structure below

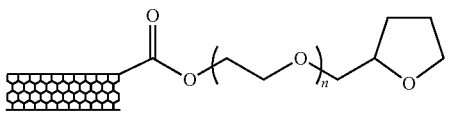

As-synthesized SWNT-PEG-THFF material contains a significant amount of impurities that are very difficult to remove, especially unreacted PEG-THFF fractions. The quality of the as-synthesized SWNT-PEG-THFF was observed by atomic force microscopy and significant amount of impurities were observed. Therefore, the continuous extraction procedure was applied to purify the as-synthesized SWNT-PEG-THFF material.

SWNT-PEG-THFF was obtained by starting with about 500 mg of carboxylic acid functionalized purified SWNTs. The pH of the aqueous media was adjusted to about 6.8 by adding approximately 1 part of concentrated HCL to about 5 parts of distilled water. At this pH, the separation between the SWNTs and the impurity fraction was approximately optimal according to the color of the separation in the vessel. The color of the solution originated from the presence of functional groups not chemically attached to SWNTs and thus may represent the main impurity fraction. At this pH the continuous extraction procedure was run for 2 weeks. AFM analysis after the CE purification showed SWNT-PEG-THFF material of significantly improved purity.

This purification process may also be adapted for the purification of other chemically functionalized CNTs, including, but not limited to, octadecylamine functionalized carbon nanotubes (ODA-SWNTs) and polyaminobenzene sulfonic acid functionalized carbon nanotubes (PABS-SWNTs).

Separation Systems and Processes

Generally, the CNT fraction obtained from the continuous extraction system 100 and/or process 200 described above includes carbon nanotubes contaminated with carbon nanoparticles (CNPs) and carboxylated carbon (CC). For example, the CNT fraction can include undispersed SWNT aggregates along with CC and CNPs in water. Thus, in some embodiments, processing is employed either in place of or in series with the continuous extraction system 100 and/or process 200 described above to further purify the CNT fraction. For example, a separation system 300 and/or process 400 can be employed to separate the CNTs from CNPs and/or CC.

Although many of the following embodiments disclosed herein describe SWNTs, the system 300 and/or process 400 may be employed with any type of carbon nanotubes, including, but not limited to, single-walled carbon nanotubes, double-walled carbon nanotubes, few-walled carbon nanotubes, and multi-walled carbon nanotubes. In another aspect, the continuous extraction process may be scaled from the laboratory to the industrial scale, with relatively low cost and complexity, in order to provide a selected output of purified CNTs.

Figure 8:
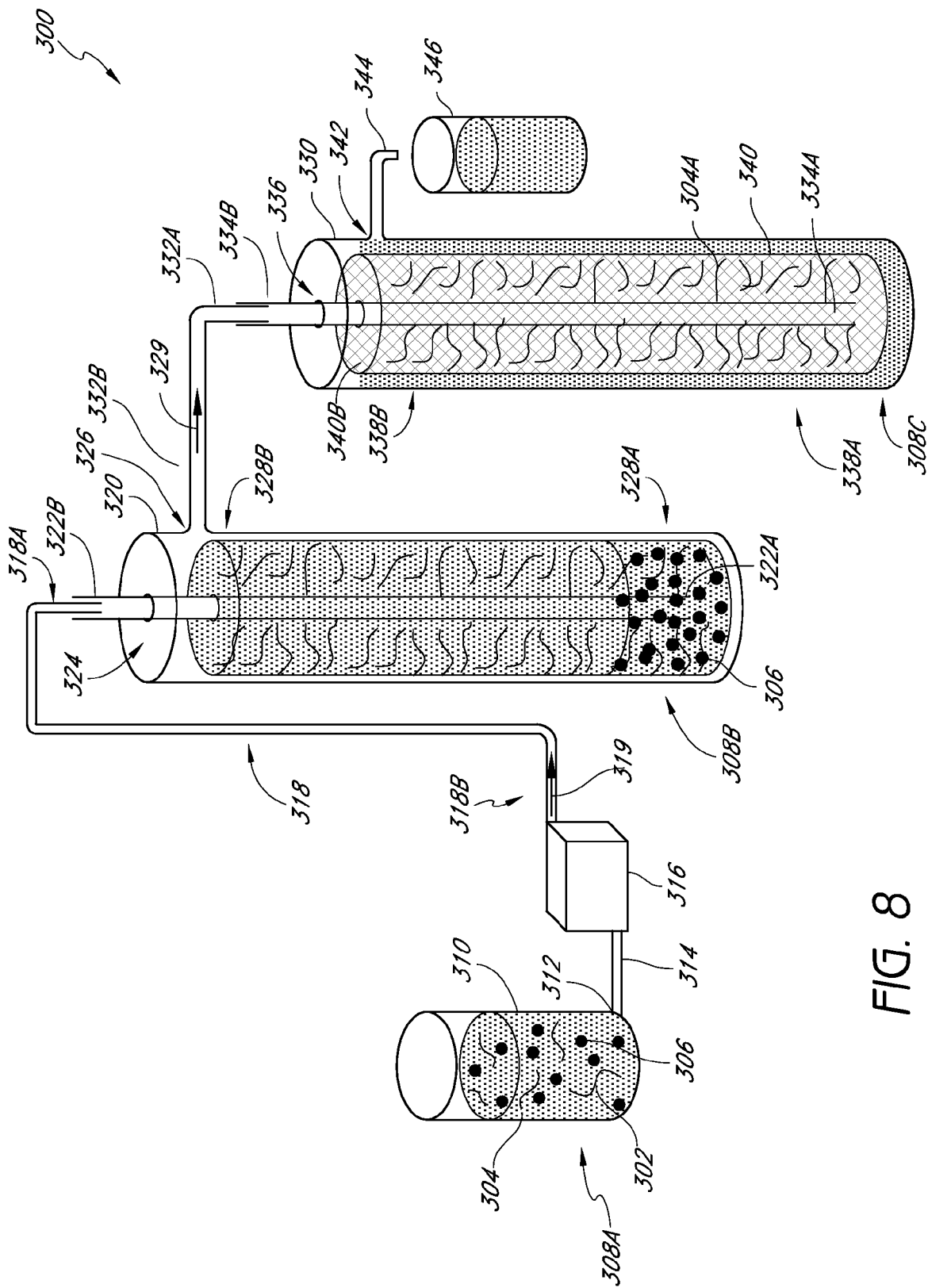
FIG. 8 schematically illustrates an embodiment of a continuous separation system for separating CNTs from a CNT, CC, and CNP mixture; (1A) separation system ready for operation; (1B) extraction of CNTs from the CNT, CC, and CNP mixture.

With regard to FIG. 8, a system for separating SWNT from impurities is illustrated. A mixture 308A comprising SWNTs 302, CC 304, and CNPs 306 can be provided to a vessel 310. In some cases, the mixture 308A is the CNF fraction obtained from the continuous extraction system 100 and/or process 200 (FIGS. 1A-2). As the mixture 308A is often heterogeneous (e.g., undispersed), in some cases the mixture 308A is agitated for a period of time to yield an approximately homogeneous dispersion of SWNTs 302, CC 304, and CNPs 306. In some embodiments, the agitation occurs by application of ultrasonic energy at a frequency in the range between about 1,000 Hz to about 100,000 Hz for a time in the range between about 10 min to about 48 h. In some embodiments, the agitation occurs by a paddle and/or a magnetic stirring system such as a magnetic stirring bar and a base housing a rotating magnet. In some cases, the mixture 308A is agitated by a bath sonicator for a time in the range between about 1 to 2 h. In some arrangements, the concentration of water in the mixture 308A is maintained in the range between about 1 to 2 g/L.

The vessel 310 may comprise a generally elongate body. In one embodiment, the vessel 310 may be approximately cylindrical with a diameter that ranges between about 1 to 10 inches and a height that ranges between about 5 to 100 inches. In one non-limiting example, the diameter of the vessel 310 may range between about 12 to 60 inches and the height of the vessel 310 may range between about 36 to 46 inches. In other embodiments, the ratio of the height of the vessel 310 to its diameter (i.e., aspect ratio) may range from approximately 1 to 1000, for example, about 1 to 12.

The vessel 310 can include an outlet 312, which can be configured to connect to a conduit 314 such that the mixture 308A can flow out of the vessel 310 and into the conduit 314. The conduit 314 in turn can connect to a liquid flow source 316. In one embodiment, the liquid flow source 316 may comprise a peristaltic pump, gravity flow, or other type of liquid flow control device. The liquid flow source 316 may be configured to provide liquid flow 319 at a rate in the range between about 0.1 to about 1000 ml/min. In some embodiments, liquid flow 319 may be provided in the range between about 1 to 100 mL/min. In some embodiments, liquid flow 319 may be provided in the range between about 1 mL/min to about 10 mL/min.

The liquid flow source 316 can be configured to connect to a distal end 318B of a conduit 318. A proximal end 318A of conduit 318 can be configured to provide the liquid flow 319 to the distal end 322B of a conduit 322. In some cases, the proximal end 318A and distal end 322B are connected by a coupling (not shown). In some embodiments, the distal end 322B is configured to receive the proximal end 318A, such as but not limited to a slip-fit or press-fit.

As illustrated, the conduit 322 can be configured to be received by an opening 324 in a vessel 320 having a first end 328A and a second end 328B. In some arrangements, the opening 324 is disposed at or near the second end 328B of the second vessel 320. The conduit 322 can extend through at least a portion of the vessel 320, such as but not limited to 10% to 90% of the length of the vessel 320. In some cases, the conduit 322 connects to the second end 328B of the vessel 320. The length of the conduit 322 may be varied, as necessary, in order to achieve a desired position within the vessel 320. The proximal end 322A of the conduit 322 can be in fluid communication with the liquid flow source 316, thereby permitting the liquid flow 319 to be received in the vessel 320.

The vessel 320 can comprise a generally elongate body of most any shape and/or size. In one embodiment, the vessel 320 may be approximately cylindrical with a diameter that ranges between about 1 to 10 inches and a height that ranges between about 5 to 100 inches. In one non-limiting example, the diameter of the vessel 320 may range between about 12 to 60 inches and the height of the vessel 320 may range between about 36 to 46 inches. In other embodiments, the ratio of the height of the vessel 320 to its diameter (i.e., aspect ratio) may range from approximately 1 to 1000, for example, about 1 to 12.

Generally, the liquid flow 319 enters the vessel 320 and pools into a mixture 308B. In some cases, a volume of solvent is present in the vessel 320 to which the liquid flow 319 is added. A variety of solvents can be employed at most any stage in the system, such as but not limited to water, dimethylformamide, tetrahydrofuran, and toluene. In some embodiments, the pH of the mixture 308B is adjusted to achieve separation of the CNPs, as is discussed below.

In some embodiments, the mixture 308B is allowed to stand and/or remain substantially unagitated for a time in the range between about 10 min to about 72 h. In some cases, the mixture 308B is allowed to stand and/or remain substantially unagitated for a time in the range between about 1 h to about 36 h. In some cases, the mixture 308B is allowed to stand and/or remain substantially unagitated overnight.

In cases in which the SWNTs 302 and CC 304 have been functionalized with carboxylic acid functional groups due to the nitric acid reflux treatment (e.g., before the continuous extraction system 100 and/or process 200), these carboxylic groups can help to disperse the SWNTs 302 and CC 304. Further, because CNPs 306 generally have a graphitized carbon structure, which does not favor formation of the carboxylic group, CNPs 306 often have poor dispersion in solvent (e.g., water) even after agitation. Thus, in some embodiments, allowing the mixture 308B to stand and/or remain substantially unagitated can result in a substantial portion of the SWNTs 302 and CC 304 being disposed at or near second end 328B (e.g., the upper end) of the vessel 320 and/or a substantial portion of the CNPs 306 settling at or near the first end 328A (e.g., the lower end) of the vessel 320. Generally, the SWNTs 302 and CC 304 disposed at or near second end 328B of the vessel 328 are in a substantially homogeneous dispersion.

In some embodiments, at least some of the SWNTs 302 and CC 304 disposed at or near second end 328B of the vessel 320 are decanted from the mixture 308B. As shown, the vessel 320 can include an opening 326 configured to receive a conduit 332 having a distal end 332B and a proximal end 332A, The proximal end 332A of the conduit 332 in turn can be received by and/or connect to a conduit 334 having distal 334B and proximal ends 334A. The conduit 334 can be configured to be received by an opening 336 in a vessel 330 having a first end 338A and a second end 338B. In some arrangements, the opening 336 is disposed at or near the second end 338B of the second vessel 330. The conduit 334 can extend through at least a portion of the vessel 330, such as but not limited to 10% to 90% of the length of the vessel 330. In some cases, the conduit 334 connects to the second end 334B of the vessel 330. The length of the conduit 334 may be varied, as necessary, in order to achieve a desired position within the vessel 330. The proximal end 334A of the conduit 334 can be in fluid communication with the second end 328B of the vessel 320, thus a decanted flow 329 including the substantially homogeneous dispersion of SWNTs 302 and CC 304 can flow though the conduits 332 and 344 and be received by the vessel 330.

The vessel 330 may comprise a generally elongate body of most any shape and/or size. In one embodiment, the vessel 330 may be approximately cylindrical with a diameter that ranges between about 1 to 10 inches and a height that ranges between about 5 to 100 inches. In one non-limiting example, the diameter of the vessel 320 may range between about 12 to 60 inches and the height of the vessel 320 may range between about 36 to 46 inches. In other embodiments, the ratio of the height of the vessel 320 to its diameter (i.e., aspect ratio) may range from approximately 1 to 1000, for example, about 1 to 12. The vessel 330 can include an outlet 342, which can be disposed at or near the second end 338 of the vessel 330.

The vessel 330 can be configured to receive a filter 340 having an exterior 340A side and an interior 340B side. In some embodiments the filter 340 includes one or more materials, such as, but not limited to, plastics (e.g., polypropylene, polyester, and the like), metals, natural materials (paper-based or wood-based material, fiber-laden materials, cotton, wool, etc.), other synthetic materials, foams, fiberglass, ceramics and/or the like. In some cases, the filter includes a nylon mesh bag having a pore size in the range of between 1 to 5 microns. In some embodiments, the vessel 330 is cylindrical and the filter includes a coaxial cylinder.

Generally, the decanted flow 329 emerges from the second end 334A of the conduit 334 and pools into a mixture 308C within the vessel 330. In some arrangements, the second end 334A of the conduit 334 is positioned so that the decanted flow 329 is encouraged to passes through the filter 340 in order to reach the outlet 342 of the vessel 330. For example, in some embodiments, the second end 334A of the conduit 334 is disposed on the interior side 340B of the filter 340, thus encouraging the decanted flow 329 to pass through the filter 340 in order to reach the outlet 342. In some cases, a volume of solvent is present in the vessel 330 to which the decanted flow 329 is added.

In embodiments in which SWNTs 302 and CC 304 have been functionalized with carboxylic groups, the dispersion of SWNTs 302 and CC 304 is dependent on the presence of the carboxylic functional groups. Accordingly, in some cases basic pH conditions disperse the SWNTs 302 and CC 304 better than acidic or neutral pH conditions. Thus, in some embodiments, the pH of the mixture 308C is modified to be basic. For example, in some cases the pH of the mixture 308C is changed to the range of between about 6 to 10. In some cases the pH of the mixture 308C is adjusted to the range of between about 8 to 9. In some embodiments, the pH change is accomplished by treatment with NaOH.

Generally, as the basic pH mixture 308C is passed through a filter 340 a portion of the SWNTs 302 are retained within the filter 340 and a portion of the CC 304 passes through the filter 340. In some embodiments, a majority of the SWNTs 302 in the mixture 308C are retained within the filter 340 and a majority of the CC 304 in the mixture 308C passes through the filter 340. In some cases, a portion of the CC 304 that passes through the filter 340 flows out the outlet 342 in the vessel 330 and is received into a receptacle 346, such as by a conduit or spout 344. In some embodiments, the SWNTs 302 retained in the filter 340 are neutralized and/or washed. For example, in some cases the SWNTs 302 retained in the filter 340 are treated to achieve an approximately neutral condition, e.g., treated with dilute HCl. In some cases, the SWNTs 302 are separated from the filter 340.

In order to provide the continuous separation system 300 with analytical capabilities, some arrangements include a monitoring system. In some cases, the monitoring system is configured to analyze, test, and/or sample at least one condition of the SWNTs 302 and/or the separated CC 304 and/or CNP 306. For example, a monitoring system can be provided to sample the decanted flow 329 at selected times during operation of the continuous separation system 300. In one embodiment, monitoring system may include evaluation (e.g., determining the presence or absence or amount of SWNTs 302, CC 304, and/or CNPs 306) by one or more of near-infrared-visible (near-IR-Vis) spectroscopy analysis or mid-infrared spectroscopy analysis. In some cases, the purification monitoring system includes one or more of a visible wavelength spectrometer, a near-infrared wavelength spectrometer, and a mid-infrared wavelength spectrometer.

FIGS. 9A-9D illustrate embodiments of a non-continuous system 300A similar to the continuous system 300 described above. Several features and components of the non-continuous system 300A are similar in form and function to those described above with respect to the continuous system 300, and have been provided with like numerals. Any features and/or components of the disclosed embodiments can be combined or used interchangeably.

Figure 9B:
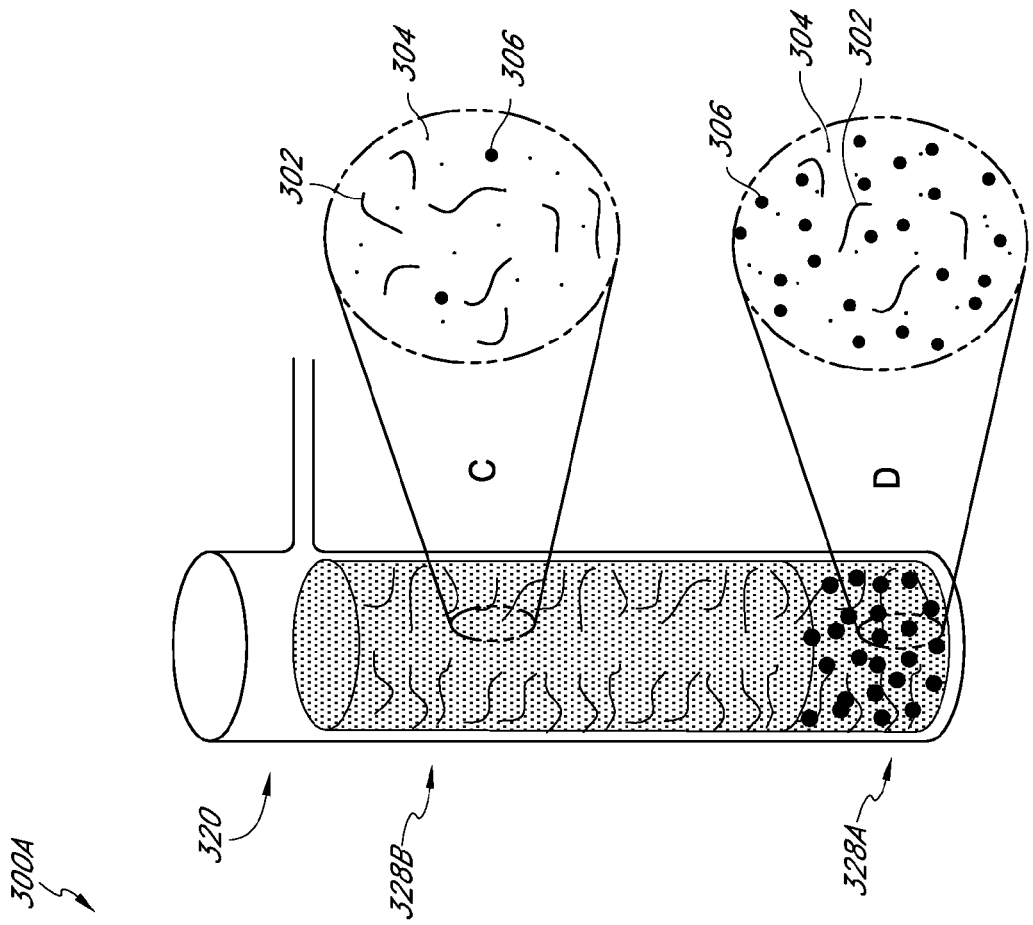
Figure 9A:
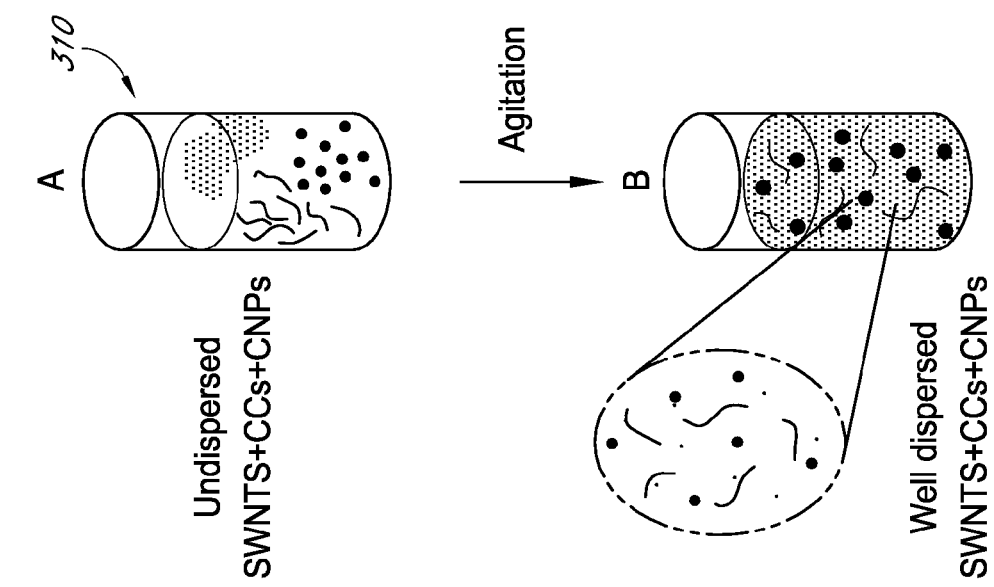

As shown, an undispersed mixture of SWNTs 302, CC 304, and CNPs 306 can be agitated for a period of time to produce a well-dispersed mixture (FIG. 9A). The well-dispersed mixture can be provided to a vessel 320 and allowed to stand and/or remain substantially unagitated for a period of time, thereby separating the CNPs to the second end 328A of the vessel 328 and the SWNTs 302 and CC 304 to the first end 328B of the vessel 328 (FIG. 9B). At least a portion of the SWNTs 302 and CC 304 can be treated using pH adjustment in order to encourage separation of the SWNTs 302 and the CC 304 (FIG. 9C). The pH adjusted SWNTs 302 and CC 304 can be provided to a filter 340, which can be configured to retain the SWNTs 302 while allowing the CC 304 to passes to an outlet 342 in the vessel 330 (FIG. 9D).

Figure 10:
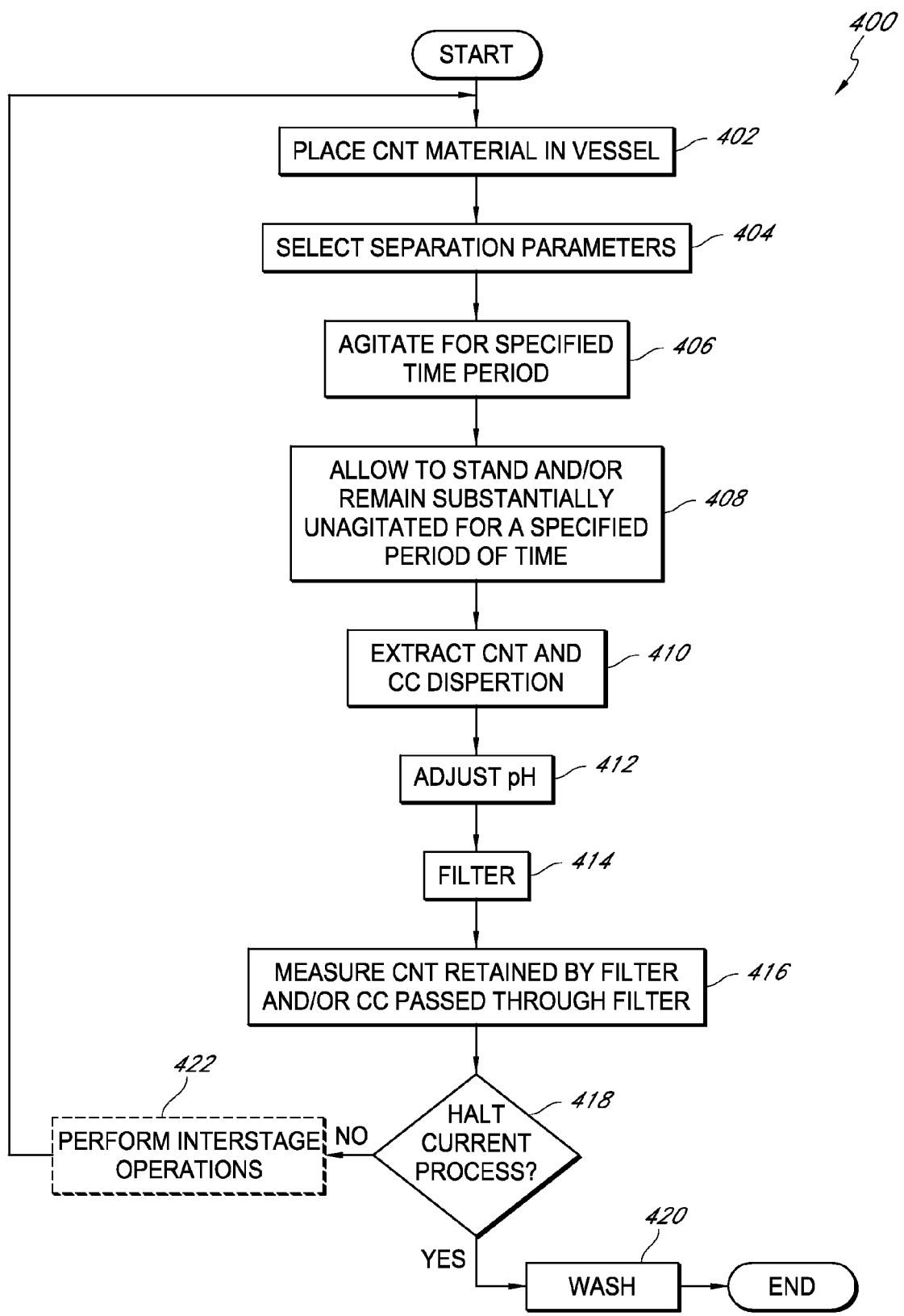
FIG. 10 is a flow diagram of one embodiment of a continuous separation system employing the system of FIGS. 8A-8B.

Turning to FIG. 10, a process 400 for separating CNTs (e.g., SWNTs) from CC and CNP is illustrated. The steps of the process 400 can employ or use interchangeably any of the features and/or components of the continuous system 300 and/or non-continuous system 300A described above. For example, the continuous system 300 describes that agitation may include sonication, thus the process 400 may also include agitation by sonication.

In a first block 402, an amount of CNT material including SWNT, CC, and CNP is provided to a vessel. In some cases, the CNT material is the result of the continuous extraction system 100 and/or process 200 described above.

In the next block 404, the separation parameters are selected. The combination of separation parameters employed in the separation system may be chosen so as to achieve separation of the SWNTs from the CC and CNPs in a desired manner. For example, the separation parameters may be chosen in order to produce an amount of SWNTs in a desired amount of time. In another embodiment, the separation parameters are selected to extract SWNTs from the CC and CNPs in a continuous process or a batch process.

In block 406, the CNT material is agitated to produce a well-dispersed mixture of SWNT, CC, and CNP. In some embodiments the agitation occurs by application of ultrasonic energy at a frequency in the range between about 10,000 Hz to about 100,000 Hz for a time in the range between about 10 min to about 48 h. In some cases, the mixture is sonicated for a time in the range between about 1 to 2 h. In some arrangements, the concentration of water in the mixture 308 is maintained in the range between about 1 to 2 g/L.

Next, in block 408, the well-dispersed mixture allowed to stand and/or remain substantially unagitated for a period of time in an elongate vessel. In some embodiments, the time period is the range between about 10 min to about 72 h. In some cases, the time period is in the range between about 1 h to about 24 h. In some cases, the time period is overnight. In some embodiments, after the period of time, a substantial portion of the SWNTs and CC is disposed in a dispersion at or near second end (e.g., the upper end) of the vessel and/or a substantial portion of the CNPs have settled at or near the first end (e.g., the lower end) of the vessel.

In block 410 at least some of the SWNTs and CC dispersion is extracted. In some embodiments, the extracted dispersion is transferred into another vessel.

Next, in block 412, the pH of the extracted dispersion is adjusted in order to encourage separation of the SWNTs and the CC. For example, in some cases the pH of the extracted dispersion is changed to the range of between about 6 to 10. Generally, the pH of the extracted dispersion is adjusted to be basic. For example, in some cases the pH of the extracted dispersion is adjusted to the range of between about 8 to 9.

In block 414, at least a portion of the pH-adjusted dispersion is passed through a filter. The filter can comprise one or more materials, such as, but not limited to, plastics (e.g., polypropylene, polyester, and the like), metals, natural materials (paper-based or wood-based material, fiber-laden materials, cotton, wool, etc.), other synthetic materials, foams, fiberglass, ceramics and/or the like. In some cases, the filter includes a nylon mesh bag having a pore size in the range of between 1 to 5 microns.

Generally, as the pH-adjusted dispersion is passed through a filter a portion of the SWNTs are retained within the filter and a portion of the CC passes through the filter. In some embodiments, a majority of the SWNTs in the dispersion are retained within the filter and a majority of the CC in the dispersion passes through the filter. In some cases, a portion of the CC that passes through the filter flows into a receptacle, such as by a conduit or spout. In some embodiments, the SWNTs are separated from the filter.

A measurement can be made in block 416. In some cases, the measurement relates to the material retained in the filter. For example, the measurement can be the ratio of SWNTs to CC and/or CNP retained in the filter. In some cases, the measurement is the purity of the SWNTs retained in the filter. In some embodiments, the measurement relates to the material passed through the filter. For instance, a spectrographic analysis of the material passed through the filter can be performed. Many other measurements are possible.

In decision block 418, a determination may be made regarding whether the current process is to be halted. In some embodiments, the decision is based at least in part on the measurement of block 416. If a determination to continue the process 400 is made in decision block 418, the material retained in the filter can be provided as the CNT material of block 402 and the process is continued for at least another iteration. By performing the process 400 additional times, additional CC and/or CNPs can be separated from the SWNTs. The process loop of blocks 402-418 may be repeated until a selected level is measured in at least one of the material retained in the filter and the material passed through the filter. In some cases, additional operations to facilitate the extraction process 400 may optionally be performed on the material to be provided to the block 402 (also referred to as interstage processes 422). For example, in some embodiments, the material to be provided to the block 402 is neutralized. In some arrangements, the material to be provided to the block 402 is dried.

If a determination to halt the process is made in decision block 418 (e.g., a selected level of achieved in at least one of the at least one of the material retained in the filter and the material passed through the filter), the process 400 moves to block 420, where the SWNTs are neutralized and/or washed. For example, in some cases the SWNTs are treated to achieve an approximately neutral condition, e.g., treated with dilute HCl.

Example

Microscopy Study of Nitric Acid Treated SWNTs Purified by Continuous Extraction Purification Process and with Removal of Carbon Nanoparticles and Carboxylated Carbon Impurities In the following example, an embodiment of the separation purification process for carbon nanotubes is discussed in greater detail. The example highlights, among other features, the high purity CNTs that may be achieved from the separation process. It may be understood, however, that this example is discussed for illustrative purposes and should not be construed to limit the disclosed embodiments.

A CNT starting material comprising nitric acid treated SWNTs was processed according to the continuous extraction purification process described above, e.g., Example 2.

A first separation stage was performed using separation parameters selected to achieve separation and removal of CNPs from the purified CNT material. In one embodiment, the purified CNT material comprised undispersed SWNT aggregates along with CC and CNPs in water. In one embodiment, the purified CNT material was sonicated in water for 1-2 hours using a bath sonicator in order to disperse the SWNTs, CC and CNPs in water. In one embodiment, the concentration of the purified CNT material in the water was maintained within the range of 1-2 g/L in order to obtain a stable dispersion. In one embodiment the sonicated purified CNT material was allowed to stand overnight in an elongate column with height in the range between about 36 to 46 inches in order to separate the CNPs from SWNTs and CC. In one embodiment, the CNP aggregates settled at or near the bottom of the column and well dispersed SWNTs and CC were present at or near the top of the column. In one embodiment, the well dispersed SWNTs and CC present at or near the top of the column were decanted as a decanted dispersion.

Figure 11B:
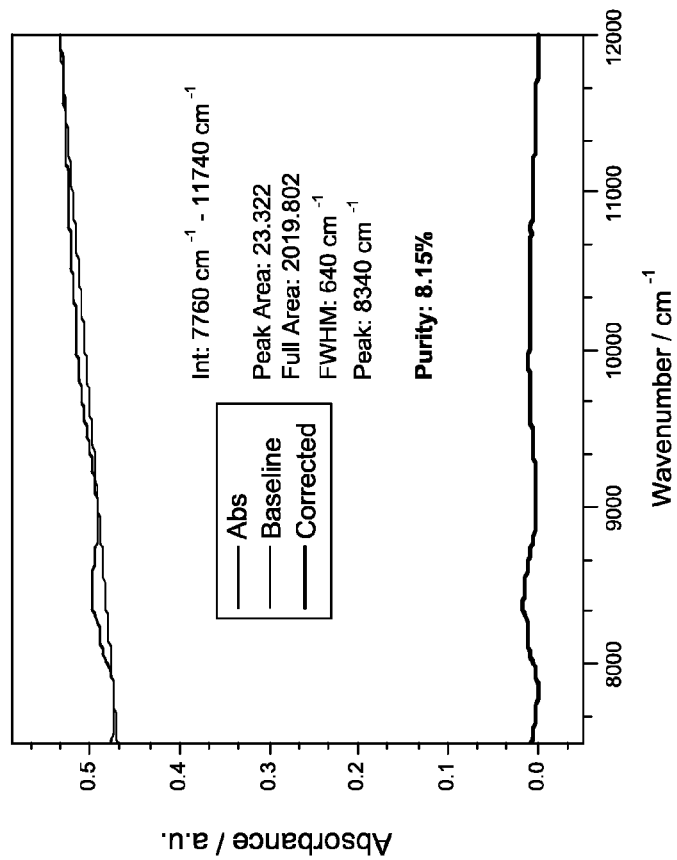
FIGS. 11A-11C relate to CNPs separated from the CNT, CC, and CNP mixture: (11A) thermogravimetric analysis; (11B) near-IR spectroscopic analysis; (11C) scanning electron microscopic image.
Figure 11A:
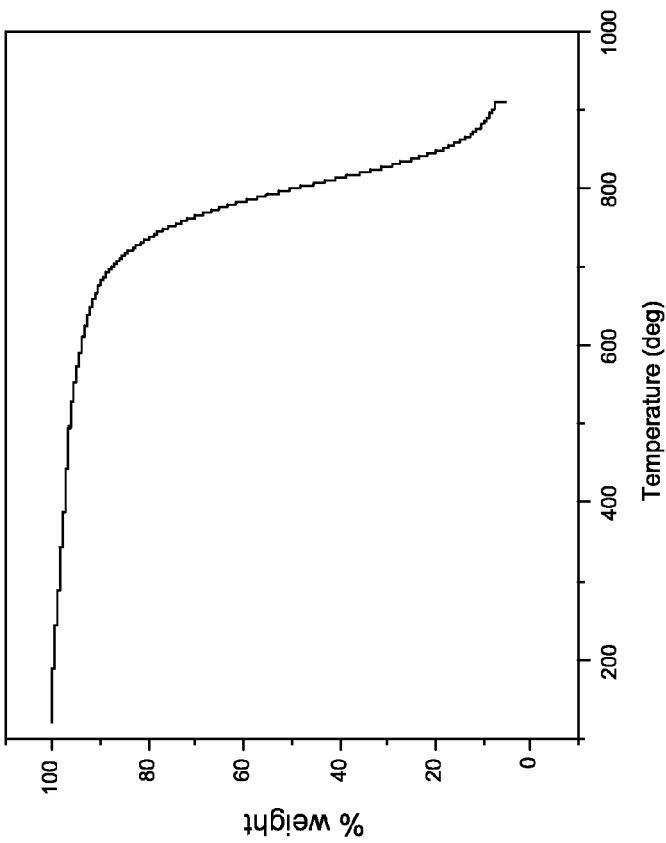
Figure 11C:
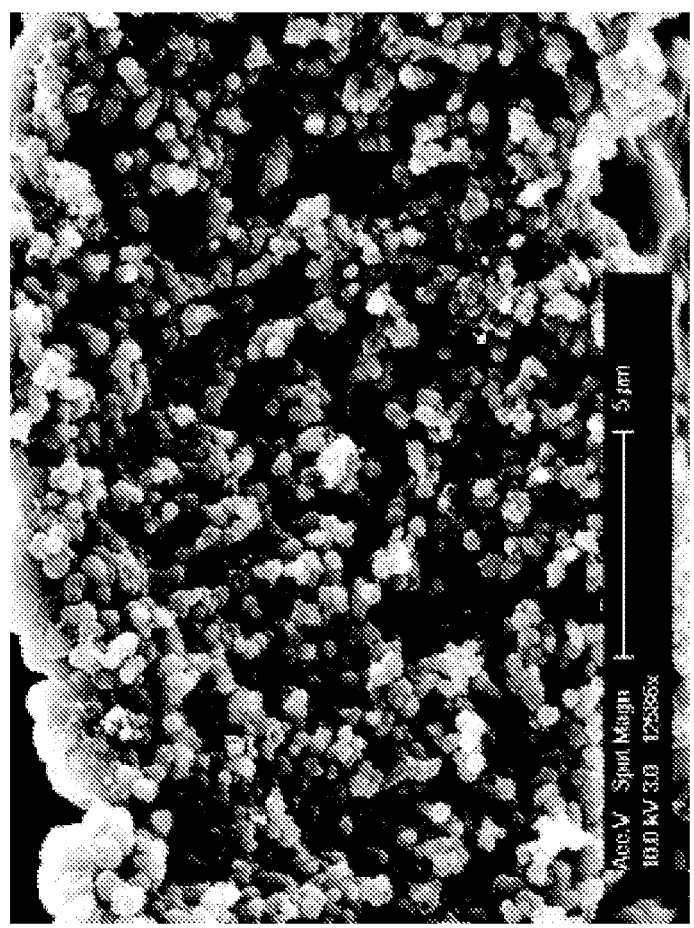

FIGS. 11A-11C show thermogravimetric (TGA), near-IR spectroscopic, and scanning electron microscopic (SEM) analysis of the material that settled at or near the bottom of the column. As shown in FIG. 11A, the TGA curve shows that the oxidation of the separated material occurs between 700-900° C., thus indicating the graphitic nature of CNPs. Indeed, FIG. 11C shows that the separated material substantially includes CNPs. The near-IR spectrum shown in FIG. 11B shows no $S_{22}$ peak associated with SWNTs, thereby indicating the absence of SWNTs in the separated material sample.

Figure 12B:
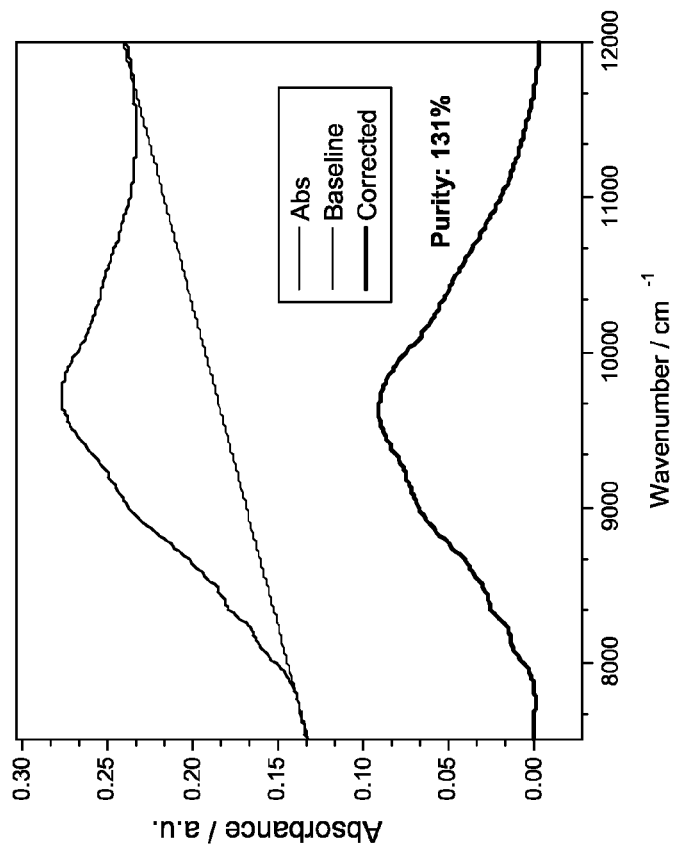
FIGS. 12A-12C relate to a CNT and CC mixture separated from the CNT, CC, and CNP mixture: (12A) thermogravimetric analysis; (12B) near-IR spectroscopic analysis; (12C) scanning electron microscopic image.
Figure 12A:
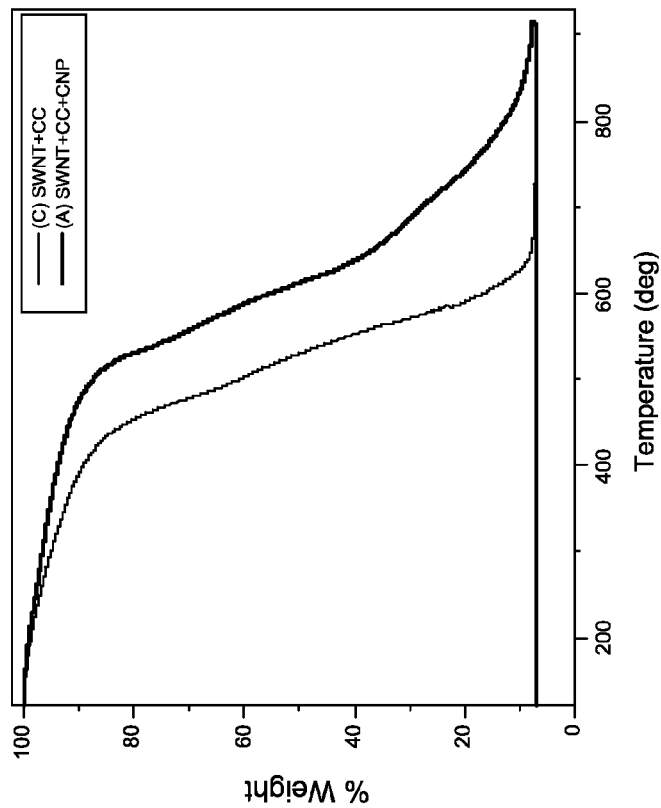
Figure 12C:
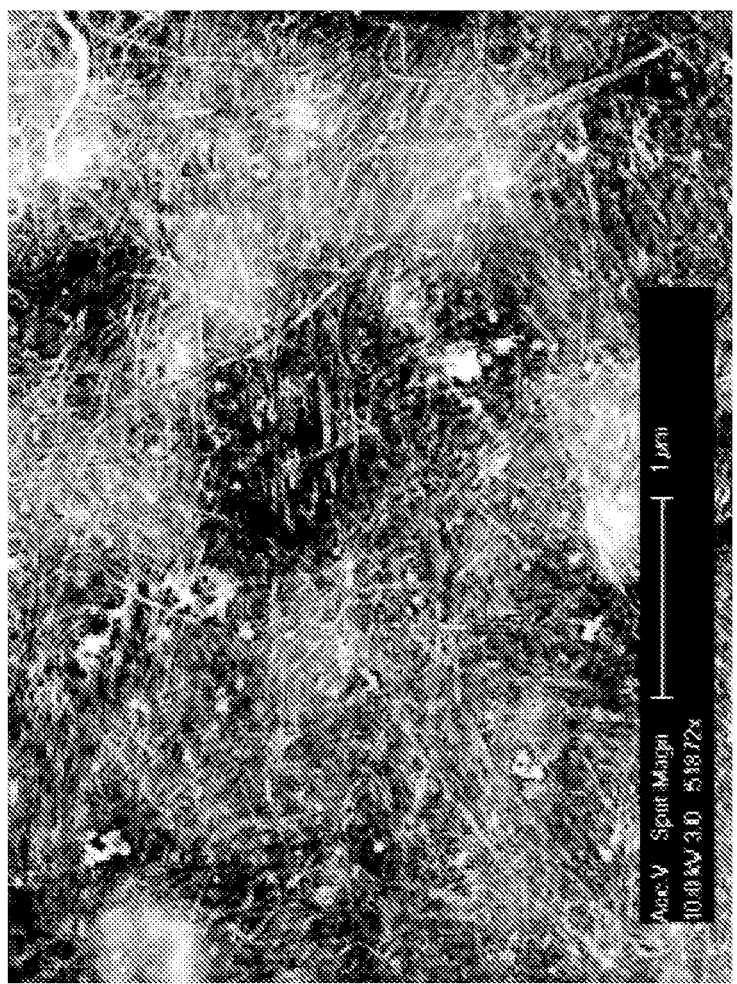

FIGS. 12A-12C show the TGA, near-IR spectroscopic, and scanning electron microscopic analysis of the decanted dispersion. The TGA curves of FIG. 12A show that the oxidation of the decanted dispersion is observed at lower temperature than the CNT starting material indicating the removal CNP. The SEM image of FIG. 12C shows that the decanted dispersion consists of SWNT and CC coating on the SWNT surface. As shown in FIG. 12C, the near-IR spectrum of the decanted dispersion shows $S_{22}$ peak associated with SWNTs indicating the presence of SWNTs in the decanted dispersion.

A second separation stage was stage performed employing separation parameters selected to achieve separation and removal of CC from the SWNTs in the decanted dispersion. In one embodiment, the decanted dispersion was subjected to a NaOH treatment to adjust the pH to the range of between about 8 to 9 to produce a pH-adjusted dispersion. In one embodiment, the pH-adjusted dispersion was passed through a nylon mesh bag. In one embodiment, the material retained in the nylon bag was neutralized with dilute HCl and washed to obtain purified SWNT.

Figure 13B:
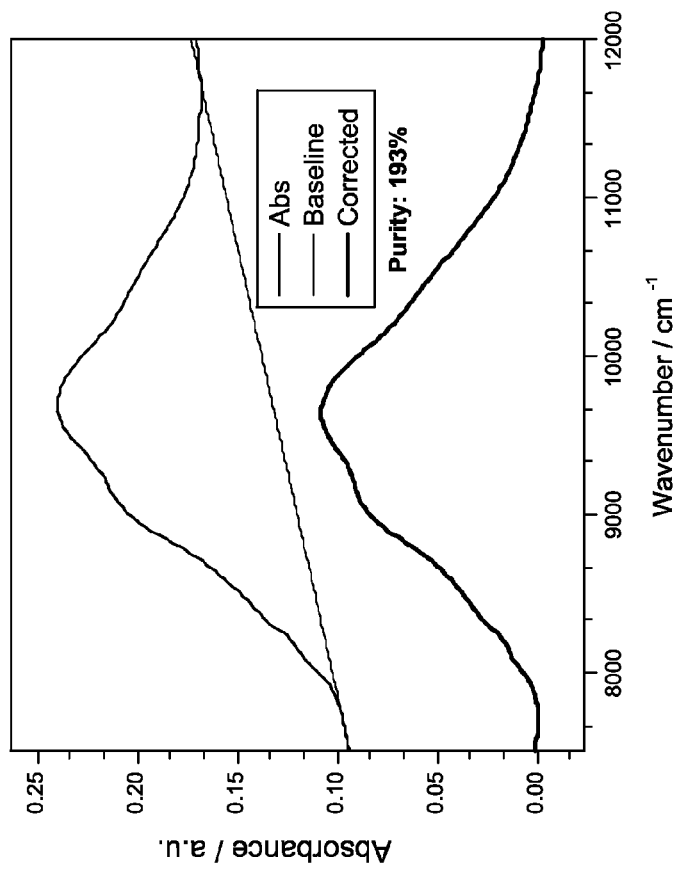
FIGS. 13A-13C relate to CNTs separated from the CNT and CC mixture: (13A) thermogravimetric analysis; (13B) near-IR spectroscopic analysis; (13C) scanning electron microscopic image.
Figure 13A:
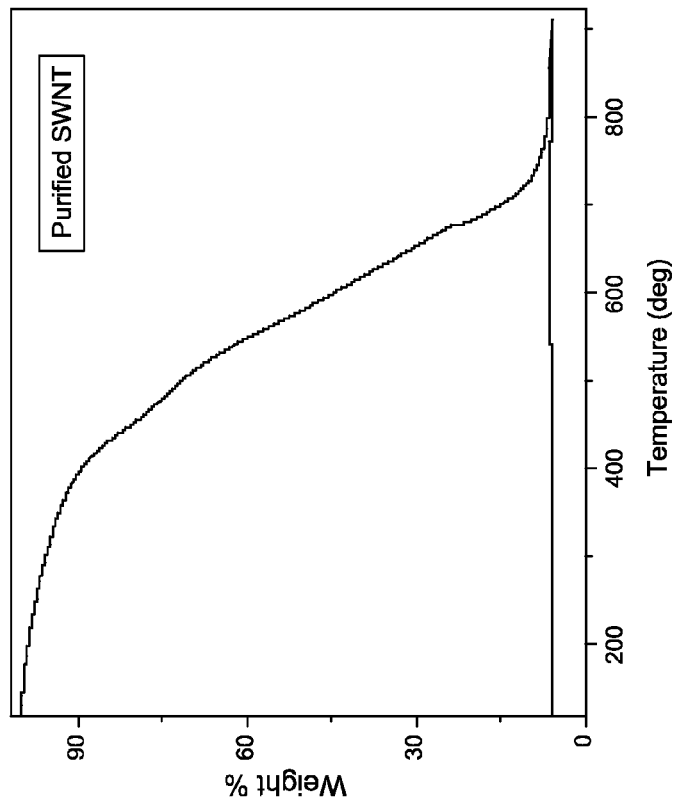
Figure 13C:
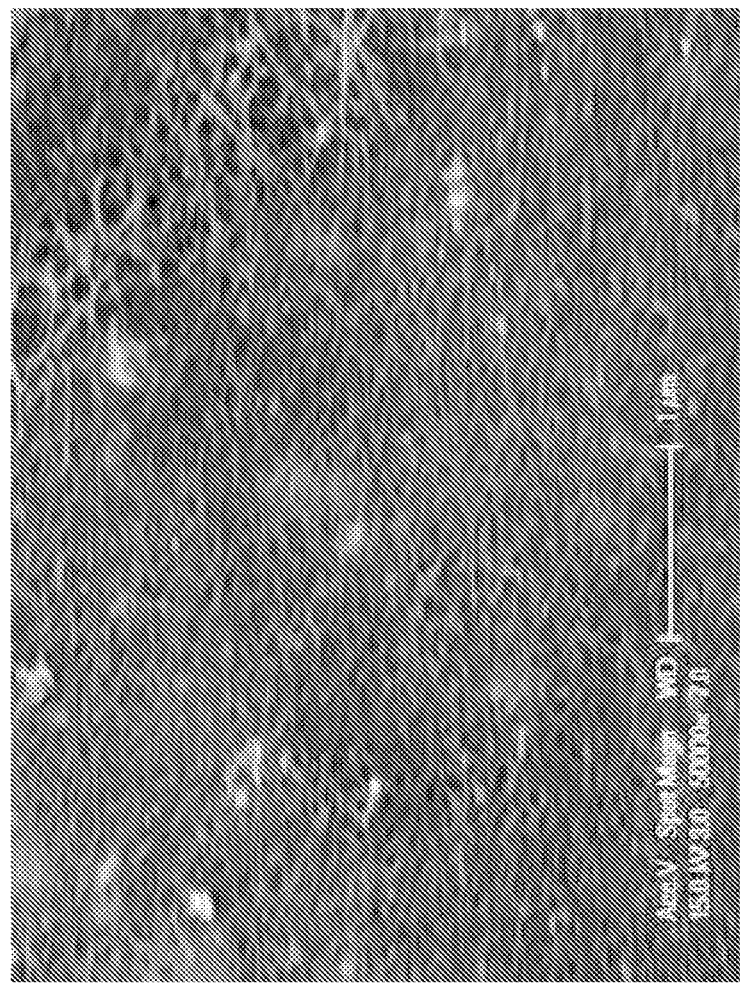

FIGS. 13A-13C show the TGA, near-IR spectrum, and SEM image of purified SWNT obtained by filtering CC from the decanted dispersion (comprising SWNTs and CC). The TGA curve of FIG. 13A shows that CNP and CC have been removed from the starting CNT material to obtain purified SWNT. FIG. 13B shows the near-IR spectrum of the purified SWNT and indicates an intense S22 peak associated with SWNTs and low background absorption corresponding to impurities. Indeed, the SEM image of FIG. 13C shows that purified SWNT substantially include SWNTs with minimal CC and CNPs.

Although the foregoing description has shown, described, and pointed out the fundamental novel features of the present teachings, it will be understood that various omissions, substitutions, and changes in the form of the detail of the apparatus as illustrated, as well as the uses thereof, may be made by those skilled in the art, without departing from the scope of the present teachings. Furthermore, the phraseology and terminology used herein is for the purpose of description and should not be regarded as limiting. No features, structure, or step disclosed herein is essential or indispensible. Consequently, the scope of the present teachings should not be limited to the foregoing discussion, but should be defined by the appended claims.

What is claimed is:

1. A method of extracting carbon nanotubes, comprising:
   providing a carbon nanotube material comprising carbon nanotubes, carbon nanoparticles, and carboxylated carbon;
   agitating the carbon nanotube material to yield a well-dispersed mixture of the carbon nanotubes, the carbon nanoparticles, and the carboxylated carbon;
   standing the well-dispersed mixture for a period of 12 to 36 hours in an elongate vessel having a lower end and an upper end, the well-dispersed mixture being substantially unagitated so as to induce the formation of a heterogeneous mixture wherein at least a portion of the carbon nanoparticles settle to the lower end by force of gravity;
   removing a dispersion comprising at least a portion of the carbon nanotubes and carboxylated carbon disposed at or near the upper end;
   adjusting the pH of the dispersion; and
   separating at least some of the carbon nanotubes from at least some of the carboxylated carbon in the dispersion.

2. The method of claim 1, wherein:
   agitating occurs for a period of between 1 to 2 hours to produce a well-dispersed mixture;
   adjusting the pH comprises adjusting the pH to between about 8 to 10; and
   separating occurs by use of a filter.

3. The method of claim 2, wherein the carbon nanotube material comprises at least one of single-walled carbon nanotubes (SWNTs), double-walled carbon nanotubes (DWNTs), few-walled carbon nanotubes (FWNTs), and multi-walled carbon nanotubes (MWNTs).

4. The method of claim 3, wherein the carbon nanotubes are chemically decorated on at least one of their sidewalls and end caps.

5. The method of claim 3, wherein carbon nanotubes comprise carboxylic acid functionalized carbon nanotubes, poly(ethylene glycol) tetrahydrofurfuryl ether functionalized carbon nanotubes (PEG-THFF-SWNTs), octadecylamine functionalized carbon nanotubes (ODA-SWNTs), and polyaminobenzene sulfonic acid functionalized carbon nanotubes (PABS-SWNTs).

6. The method of claim 1, wherein agitating occurs for a period of between 10 minutes to 48 hours.

7. The method of claim 1, wherein agitating the carbon nanotube material comprises stirring.

8. The method of claim 6, wherein stirring occurs at a rate of 5 to 1200 rotations per minute.

9. The method of claim 6, wherein stirring is accomplished with a magnetic stirring system.

10. The method of claim 6, wherein stirring is accomplished with a paddle.

11. The method of claim 1, wherein separating at least some of the carbon nanotubes from at least some of the carboxylated carbon in the dispersion comprises passing the dispersion through a filter, wherein the filtrate comprises a greater percentage of carboxylated carbon than carbon nanotubes.

12. The method of claim 1, wherein adjusting the pH comprises adjusting the pH to between 8 to 10.

13. A method of extracting carbon nanotubes, comprising:
providing a carbon nanotube material comprising carbon nanotubes, carbon nanoparticles, and carboxylated carbon;
agitating the carbon nanotube material for a period of between 1 to 2 hours to yield a well-dispersed mixture of the carbon nanotubes, the carbon nanoparticles, and the carboxylated carbon;
standing the well-dispersed mixture in an elongate vessel having a lower end and an upper end, the well-dispersed mixture being substantially unagitated so as to induce the formation of a heterogeneous mixture wherein at least a portion of the carbon nanoparticles settle to the lower end by force of gravity;
removing a dispersion comprising at least a portion of the carbon nanotubes and carboxylated carbon disposed at or near the upper end;
adjusting the pH of the dispersion; and
separating at least some of the carbon nanotubes from at least some of the carboxylated carbon in the dispersion.

14. The method of claim 13, wherein standing occurs for a period of 1 to 36 hours.

15. The method of claim 13, wherein agitating the carbon nanotube material comprises stirring.

16. The method of claim 13, wherein separating at least some of the carbon nanotubes from at least some of the carboxylated carbon in the dispersion comprises passing the dispersion through a filter, wherein the filtrate comprises a greater percentage of carboxylated carbon than carbon nanotubes.

17. The method of claim 13, wherein adjusting the pH comprises adjusting the pH to between 8 to 9.

18. The method of claim 13, wherein:
standing occurs for a period of between 12 to 36 hours;
adjusting the pH comprises adjusting the pH to between 8 to 10; and
separating occurs by use of a filter.

19. The method of claim 15, wherein the carbon nanotube material comprises at least one of single-walled carbon nanotubes (SWNTs), double-walled carbon nanotubes (DWNTs), few-walled carbon nanotubes (FWNTs), and multi-walled carbon nanotubes (MWNTs).

20. The method of claim 19, wherein the carbon nanotubes are chemically decorated on at least one of their sidewalls and end caps.

21. The method of claim 19, wherein carbon nanotubes comprise carboxylic acid functionalized carbon nanotubes, poly(ethylene glycol) tetrahydrofurfuryl ether functionalized carbon nanotubes (PEG-THFF-SWNTs), octadecylamine functionalized carbon nanotubes (ODA-SWNTs), and polyaminobenzene sulfonic acid functionalized carbon nanotubes (PABS-SWNTs).

* * * * *